(12) United States Patent
Zablocki et al.

(10) Patent No.: US 6,677,336 B2
(45) Date of Patent: Jan. 13, 2004

(54) SUBSTITUTED PIPERAZINE COMPOUNDS

(75) Inventors: Jeff Zablocki, Mountain View, CA (US); Elfatih Elzein, Fremont, CA (US); Grigory Nudelman, Pacifica, CA (US); Tim Marquart, San Francisco, CA (US); Brent K. Blackburn, Los Altos, CA (US); Venkata P. Palle, Mountain View, CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 0 days.

(21) Appl. No.: 09/791,134

(22) Filed: Feb. 22, 2001

(65) Prior Publication Data

US 2002/0016463 A1 Feb. 7, 2002

Related U.S. Application Data

(60) Provisional application No. 60/184,182, filed on Feb. 22, 2000.

(51) Int. Cl.[7] .................... A61K 31/495; A61K 31/496; C07D 241/08; C07D 241/04; C07D 403/10
(52) U.S. Cl. .............. 514/235.8; 514/254.01; 514/255.02; 514/249; 514/412; 544/121; 544/372; 544/384; 544/400; 544/231; 544/353; 548/543
(58) Field of Search ................. 544/384, 400, 544/121, 372; 514/255.02, 235.8, 254.01

(56) References Cited

U.S. PATENT DOCUMENTS

| | | | |
|---|---|---|---|
| 4,558,129 A | | 12/1985 | Kluge et al. |
| 4,567,264 A | * | 1/1986 | Kluge et al. |
| 4,766,125 A | * | 8/1988 | Van Daele |
| 5,472,707 A | | 12/1995 | Samuels et al. |
| 5,506,229 A | * | 4/1996 | Dow et al. |
| 5,670,171 A | | 9/1997 | Santus et al. |
| 5,906,988 A | | 5/1999 | Dow |

FOREIGN PATENT DOCUMENTS

| | | |
|---|---|---|
| CA | 2054544 | 5/1992 |
| EP | 0 068 544 | 1/1983 |
| EP | 0 143 016 | 5/1985 |
| EP | 0 407 780 | 1/1991 |
| EP | 0 483 932 | 6/1992 |
| JP | 03 141258 A | 6/1991 |

OTHER PUBLICATIONS

Pepine et al., "A Controlled Trial with a Novel Anti–Ischemic Agent, Ranolazine, in Chronic Stable Angina Pectoris That is Responsive to Conventional Antianginal Agents", *American Journal of Cardiology*, vol. 84, pp. 46–50 (1999).

* cited by examiner

*Primary Examiner*—Emily Bernhardt
(74) *Attorney, Agent, or Firm*—McDonnell Boehnen Hulbert & Berghoff

(57) ABSTRACT

Novel compounds of the general formula:

I and pharmaceutically acceptable acid addition salts thereof, wherein the compounds are useful in therapy to protect skeletal muscles against damage resulting from trauma or to protect skeletal muscles subsequent to muscle or systemic diseases such as intermittent claudication, to treat shock conditions, to preserve donor tissue and organs used in transplants, in the treatment of cardiovascular diseases including atrial and ventricular arrhythmias, Prinzmetal's (variant) angina, stable angina, and exercise induced angina, congestive heart disease, and myocardial infarction.

34 Claims, No Drawings

SUBSTITUTED PIPERAZINE COMPOUNDS

BACKGROUND OF THE INVENTION

This application claims priority to U.S. patent application Ser. No. 60/184,182 filed on Feb. 22, 2000, the specification of which is incorporated herein by reference.

1. Field of the Invention

The present invention is concerned with substituted piperazine compounds, therapeutic dosage forms including one or more of the compounds, and methods for treating diseases in mammals, and in particular, in a human in a therapy selected from the group including protecting skeletal muscles against damage resulting from trauma, protecting skeletal muscles subsequent to muscle or systemic diseases such as intermittent claudication, to treat shock conditions, to preserve donor tissue and organs used in transplants, and to treat cardiovascular diseases including atrial and ventricular arrhythmias, Prinzmetal's (variant) angina, stable angina, and exercise induced angina, congestive heart disease, and myocardial infarction.

2. Description of the Art

U.S. Pat. No. 4,567,264, the specification of which is incorporated herein by reference, discloses a class of substituted piperazine compounds that includes a compound known as ranolazine, (±)-N-(2,6-dimethylphenyl)-4-[2-hydroxy-3-(2-methoxyphenoxy)-propyl]-1-piperazineacetamide, and its pharmaceutically acceptable salts, and their use in the treatment of cardiovascular diseases, including arrhythmias, variant and exercise-induced angina, and myocardial infarction.

U.S. Pat. No. 5,506,229, which is incorporated herein by reference, discloses the use of ranolazine and its pharmaceutically acceptable salts and esters for the treatment of tissues experiencing a physical or chemical insult, including cardioplegia, hypoxic or reperfusion injury to cardiac or skeletal muscle or brain tissue, and for use in transplants. In particular, ranolazine is particularly useful for treating arrhythmias, variant and exercise-induced angina, and myocardial infarction by partially inhibiting cardiac fatty acid oxidation. Conventional oral and parenteral ranolazine formulations are disclosed, including controlled release formulations. In particular, Example 7D of U.S. Pat. No. 5,506,229 describes a controlled release formulation in capsule form comprising microspheres of ranolazine and microcrystalline cellulose coated with release controlling polymers.

Despite the important discovery that ranolazine is a very useful cardiac therapeutic agent, there remains a need for compounds that are partial fatty acid oxidation inhibitors that have a half-life greater than ranolazine and that have activities as least similar to ranolazine.

SUMMARY OF THE INVENTION

This invention includes novel substituted piperazine compounds that are partial fatty acid oxidation inhibitors with good therapeutic half-lives.

This invention also includes novel substituted piperazine compounds that can be administered to a mammal to protect skeletal muscles against damage resulting from trauma, to protecting skeletal muscles subsequent to muscle or systemic diseases such as intermittent claudication, to treat shock conditions, to preserve donor tissue and organs used in transplants, and to treat cardiovascular diseases including atrial and ventricular arrhythmias, Prinzmetal's (variant) angina, stable angina, and exercise induced angina, congestive heart disease, and myocardial infarction.

This invention includes a class of substituted piperazine compounds having the following formula:

I

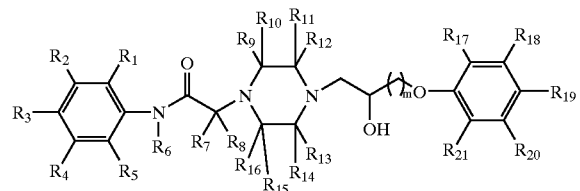

wherein
m=1, 2;
wherein
$R_1$, $R_2$, $R_3$, $R^4$ and $R^5$ are each independently selected from the group consisting of hydrogen, halo, $CF_3$, $OR^{22}$ and $C_{1-4}$ alkyl and wherein $R^{22}$ is a $C_{1-3}$ alkyl;
$R^6$, $R^7$ and $R^8$ each independently selected from the group consisting of hydrogen and $C_{1-3}$ alkyl;
$R^9$, $R^{10}$, $R^{11}$, $R^{12}$, $R^{13}$, $R^{14}$, $R^{15}$ and $R^{16}$ are each independently selected from the group consisting of hydrogen and $C_{1-4}$ alkyl, or $R^9$ and $R^{10}$ may together form a carbonyl, or $R^{11}$ and $R^{12}$ may together form a carbonyl, or $R^{13}$ and $R^{14}$ may together form a carbonyl, or $R^{15}$ and $R^{16}$ may together form a carbonyl wherein $R_{11}$ and $R_{13}$ or $R_9$ and $R_{15}$ or $R_9$ and $R_{11}$ or $R_{11}$ and $R_{15}$ or $R_9$ and $R_{13}$ may join together to form a bridging ring system wherein the two R groups together comprise of from 1 to 4 carbon atoms with the proviso that $R^9$, $R^{10}$, $R^{11}$, $R^{12}$, $R^{13}$, $R^{14}$, $R^{15}$ and $R^{16}$ are not all simultaneously hydrogen.

$R^{17}$, $R^{18}$, $R^{19}$, $R^{20}$ and $R^{21}$ are each independently selected from the group consisting of hydrogen, halo, $CF_3$, CN, $OR^{22}$, $S(O)R^{22}$, $SO_2R^{22}$, $SON(R^{22})_2$, $CON(R^{22})_2$, $C_{1-4}$ alkyl wherein $R^{22}$ is $C_{1-3}$ alkyl, or $R^{17}$ and $R^{18}$ may together form —CH=CH—CH=CH—, or $R^{18}$ and $R^{19}$ may together form —OCH$_2$O—.

In another embodiment, this invention is a substituted piperazine compound selected from the group consisting of N-(2,6-dimethylphenyl)-2-{4-[2-hydroxy-3-(2-methoxyphenoxy)propyl]-3-oxopiperazinyl}acetamide, N-(2,6-dimethylphenyl)-2-{4-[2-hydroxy-3-(2-methoxyphenoxy)propyl]-3,5-dimethylpiperazinyl}acetamide, 2-{(5S,2R)-4-[2-hydroxy-3-(2-methoxyphenoxy)propyl]-2,5-dimethylpiperazinyl}-N-(2,6-dimethylphenyl)acetamide, 2-{2,5-diaza-5-[2-hydroxy-3-(2-methoxyphenoxy)propyl]bicyclo[4.4.0]dec-2-yl}-N-(2,6-dimethylphenyl)acetamide, N-(2,6-dimethylphenyl)-2-{4-[2-hydroxy-3-(2-methoxyphenoxy)propyl]-3-oxopiperazinyl}acetamide, N-(2,6-dimethylphenyl)-2-{4-[2-hydroxy-3-(2-methoxyphenoxy)propyl]-3,3-dimethylpiperazinyl}acetamide, 2-{5-[(2S)-2-hydroxy-3-(2-methoxyphenoxy)propyl](1S,4S)-2,5-diazabicyclo[2.2.1]hept-2-yl}-N-(2,6-dimethylphenyl)acetamide, N-(2,6-dimethylphenyl)-2-{4-[2-hydroxy-4-(2-methoxyphenoxy)butyl]-piperazinyl}acetamide, N-(2,6-dimethylphenyl)-2-{4-[4-(4-fluorophenoxy)-2-hydroxybutyl]-piperazinyl}acetamide, 2-(4-{4-[4-(tert-butyl)phenoxy]-2-hydroxybutyl}piperazinyl)-N-(2,6-dimethylphenyl)acetamide, N-(2,6-dimethylphenyl)-2-{4-[2-hydroxy-4-(4-phenylphenoxy)butyl]piperazinyl}acetamide, N-(2,6-dimethylphenyl)-2-{4-[2-hydroxy-4-(4-methoxyphenoxy)butyl]-piperazinyl}acetamide, 2-{(3S)-4-[(2S)-3-(2-fluorophenoxy)-2-hydroxypropyl]-

3-methylpiperazinyl}-N-(2,6-dimethylphenyl) acetamide, 2-{(3S)-4-[(2S)-3-(2-fluorophenoxy)-2-hydroxypropyl]-3-methylpiperazinyl}-N-(2,6-dichlorophenyl)acetamide, 2-{(3S)-4-[(2S)-3-(2-fluorophenoxy)-2-hydroxypropyl]-3-methylpiperazinyl}-N-(4-sulfamoylphenyl)acetamide, 2-{(3S)-4-[(2S)-3-(2-fluorophenoxy)-2-hydroxypropyl]-3-methylpiperazinyl}-N-(5-methoxy-3-(trifluoromethyl)phenyl]acetamide, 2-{(3S)-4-[(2S)-3-(2-fluorophenoxy)-2-hydroxypropyl]-3-methylpiperazinyl}-N-indan-5-ylacetamide, 2-{(3S)-4-[(2S)-3-(2-fluorophenoxy)-2-hydroxypropyl]-3-methylpiperazinyl}-N-naphthylacetamide, 2-{(3S)-4-[(2S)-3-(2-fluorophenoxy)-2-hydroxypropyl]-3-methylpiperazinyl}-N-(4-chloronaphthyl)acetamide, 2-{(3S)-4-[(2S)-3-(2-fluorophenoxy)-2-hydroxypropyl]-3-methylpiperazinyl}-N-(2-pyrrolylphenyl)acetamide, 2-{(3S)-4-[(2S)-3-(2-fluorophenoxy)-2-hydroxypropyl]-3-methylpiperazinyl}-N-phenylacetamide, 2-{(3S)-4-[(2S)-3-(2-fluorophenoxy)-2-hydroxypropyl]-3-methylpiperazinyl}-N-(2-chlorophenyl)acetamide, 2-{(3S)-4-[(2S)-3-(2-fluorophenoxy)-2-hydroxypropyl]-3-methylpiperazinyl}-N-(2-chloro-4-methylphenyl) acetamide, 2-{(3S)-4-[(2S)-3-(2-fluorophenoxy)-2-hydroxypropyl]-3-methylpiperazinyl}-N-[2-(1-methylvinyl)phenyl]acetamide, 2-{(3S)-4-[(2S)-3-(2-fluorophenoxy)-2-hydroxypropyl]-3-methylpiperazinyl}-N-(2-methylphenyl)acetamide, 2-{(3S)-4-[(2S)-3-(2-fluorophenoxy)-2-hydroxypropyl]-3-methylpiperazinyl}-N-[6-methyl-2-(methylethyl)phenyl]acetamide, 2-{(3S)-4-[(2S)-3-(2-fluorophenoxy)-2-hydroxypropyl]-3-methylpiperazinyl}-N-(3-methylthiophenyl)acetamide, 2-{(3S)-4-[(2S)-3-(2-fluorophenoxy)-2-hydroxypropyl]-3-methylpiperazinyl}-N-(4-chloro-2-methoxy-5-methylphenyl)acetamide, 2-{(3S)-4-[(2S)-3-(2-fluorophenoxy)-2-hydroxypropyl]-3-methylpiperazinyl}-N-[4-(dimethylamino)phenyl] acetamide, 2-{(3S)-4-[(2S)-3-(2-fluorophenoxy)-2-hydroxypropyl]-3-methylpiperazinyl}-N-(2,4-dimethoxyphenyl)acetamide, 2-{(3S)-4-[(2S)-3-(2-fluorophenoxy)-2-hydroxypropyl]-3-methylpiperazinyl}-N-(3,4-dichlorophenyl)acetamide, 2-{(3S)-4-[(2S)-3-(2-fluorophenoxy)-2-hydroxypropyl]-3-methylpiperazinyl}-N-(4-chlorophenyl)acetamide, 2-{(3S)-4-[(2S)-3-(2-fluorophenoxy)-2-hydroxypropyl]-3-methylpiperazinyl}-N-(3-chlorophenyl)acetamide, 2-{(3S)-4-[(2S)-3-(2-fluorophenoxy)-2-hydroxypropyl]-3-methylpiperazinyl}-N-(3,5-dichlorophenyl) acetamide, 2-{(3S)-4-[(2S)-3-(2-fluorophenoxy)-2-hydroxypropyl]-3-methylpiperazinyl}-N-(4-methoxyphenyl)acetamide, 2-{(3S)-4-[(2S)-3-(2-fluorophenoxy)-2-hydroxypropyl]-3-methylpiperazinyl}-N-(4-methylphenyl)acetamide, 2-{(3S)-4-[(2S)-3-(2-fluorophenoxy)-2-hydroxypropyl]-3-methylpiperazinyl}-N-(3-methylphenyl)acetamide, 2-{(3S)-4-[(2S)-3-(2-fluorophenoxy)-2-hydroxypropyl]-3-methylpiperazinyl}-N-(4-fluorophenyl)acetamide, 2-{(3S)-4-[(2S)-3-(2-fluorophenoxy)-2-hydroxypropyl]-3-methylpiperazinyl}-N-(4-cyanophenyl)acetamide, 2-{(3S)-4-[(2S)-3-(2-fluorophenoxy)-2-hydroxypropyl]-3-methylpiperazinyl}-N-(4-acetylphenyl)acetamide, 2-{(3S)-4-[(2S)-3-(2-fluorophenoxy)-2-hydroxypropyl]-3-methylpiperazinyl}-N-(2-methoxyphenyl)acetamide, 2-{(3S)-4-[(2S)-3-(2-fluorophenoxy)-2-hydroxypropyl]-3-methylpiperazinyl}-N-[4-(trifluoromethyl)phenyl] acetamide, 2-{(3S)-4-[(2S)-3-(2-fluorophenoxy)-2-hydroxypropyl]-3-methylpiperazinyl}-N-[4-chloro-3-(trifluoromethyl)phenyl]acetamide, 2-{(3S)-4-[(2S)-3-(2-fluorophenoxy)-2-hydroxypropyl]-3-methylpiperazinyl}-N-(3,5-dimethoxyphenyl) acetamide, 2-{(3S)-4-[(2S)-3-(2-fluorophenoxy)-2-hydroxypropyl]-3-methylpiperazinyl}-N-(4-morpholin-4-ylphenyl)acetamide, 2-{(3S)-4-[(2S)-3-(2-fluorophenoxy)-2-hydroxypropyl]-3-methylpiperazinyl}-N-(3-fluoro-4-methoxyphenyl) acetamide, 2-{(3S)-4-[(2S)-3-(2-fluorophenoxy)-2-hydroxypropyl]-3-methylpiperazinyl}-N-(3,4,5-trimethoxyphenyl)acetamide, 2-{(3S)-4-[(2S)-3-(2-fluorophenoxy)-2-hydroxypropyl]-3-methylpiperazinyl}-N-(3,4-dimethoxyphenyl) acetamide, 2-{(3S)-4-[(2S)-3-(2-fluorophenoxy)-2-hydroxypropyl]-3-methylpiperazinyl}-N-(4-chloro-2-fluorophenyl)acetamide, and 2-{(3S)-4-[(2S)-3-(2-fluorophenoxy)-2-hydroxypropyl]-3-methylpiperazinyl}-N-[2-(hydroxymethyl-6-methylphenyl]acetamide.

In yet another embodiment, this invention is a method for administering one or more composition of this invention to a mammal in a treatment selected from the group consisting of protecting skeletal muscles against damage resulting from trauma, protecting skeletal muscles subsequent to muscle or systemic diseases such as intermittent claudication, to treat shock conditions, to preserve donor tissue and organs used in transplants, and to treat cardiovascular diseases including atrial and ventricular arrhythmias, Prinzmetal's (variant) angina, stable angina, and exercise induced angina, congestive heart disease, and myocardial infarction.

DETAILED DESCRIPTION OF THE INVENTION

This invention concerns substituted piperazine compounds having the following formula:

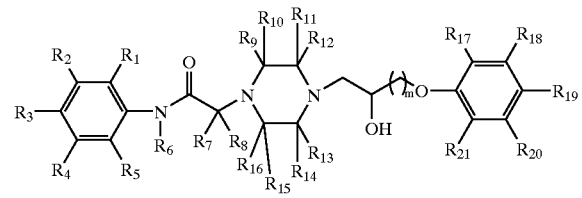

wherein
m=1, 2;

$R_1$, $R_2$, $R_3$, $R^4$ and $R^5$ are each independently selected from the group consisting of hydrogen, halo, $CF_3$, $OR^{22}$ and $C_{1-4}$ alkyl and wherein $R^{22}$ is a $C_{1-3}$ alkyl;

$R^6$, $R^7$ and $R^8$ each independently selected from the group consisting of hydrogen and $C_{1-3}$ alkyl;

$R^9$, $R^{10}$, $R^{11}$, $R^{12}$, $R^{13}$, $R^{14}$, $R^{15}$ and $R^{16}$ are each independently selected from the group consisting of hydrogen and $C_{1-4}$ alkyl, or $R^9$ and $R^{10}$ may together form a carbonyl, or $R^{11}$ and $R^{12}$ may together form a carbonyl, or $R^{13}$ and $R^{14}$ may together form a carbonyl, or $R^{15}$ and $R^{15}$ may together form a carbonyl wherein $R_{11}$ and $R_{13}$ or $R_9$ and $R_{15}$ or $R_9$ and $R_{11}$ or $R^{11}$ and $R_{15}$ or $R_9$ and $R_{13}$ may join together to form a bridging ring system wherein the two R groups together comprise of from 1 to 4 carbon atoms with the proviso that $R^9$, $R^{10}$, $R^{11}$, $R^{12}$, $R^{13}$, $R^{14}$, $R^{15}$ and $R^{16}$ are not all simultaneously hydrogen.

$R^{17}$, $R^{18}$, $R^{19}$, $R^{20}$ and $R^{21}$ are each independently selected from the group consisting of hydrogen, halo, $CF_3$, CN, $OR^{22}$, $S(O)R^{22}$, $SO_2R^{22}$, $SON(R^{22})_2$, $CON(R^{22})_2$, $C_{1-4}$ alkyl wherein $R^{22}$ is $C_{1-3}$ alkyl, or $R^{17}$ and $R^{18}$ may together form —CH=CH—CH=CH—, or $R^{18}$ and $R^{19}$ may together form —OCH$_2$O—.

In more preferred compositions of this invention $R_1$, $R_2$, $R_3$, $R^4$ and $R^5$ are each selected from the group consisting of hydrogen, halo, $CF_3$, $OR^{22}$ and $C_{1-4}$ alkyl where $R^{22}$ is a $C_{1-3}$ alkyl; $R^6$ is selected from hydrogen and methyl; $R^7$, $R^8$, $R^9$, $R^{10}$, $R^{11}$, $R^{12}$, $R^{13}$, $R^{14}$, $R^{15}$ and $R^{16}$ are each independently selected from hydrogen and methyl or $R^9$ and $R^{10}$ may together form a carbonyl, or $R^{13}$ and $R^{14}$ may together form a carbonyl with the proviso that $R^9$, $R^{10}$, $R^{11}$, $R^{12}$, $R^{13}$, $R^{14}$, $R^{15}$ and $R^{16}$ are not all simultaneously hydrogen.; $R^{17}$, $R^{18}$, $R^{19}$, $R^{20}$ and $R^{21}$ are each independently selected from the group consisting of hydrogen, halo, $CF_3$, $OR^{22}$, $C_{1-3}$ alkyl wherein $R^{22}$ is $C_{1-3}$ alkyl, or $R^{17}$ and $R^{18}$ may together form —CH=CH—CH=CH—, or $R^{18}$ and $R^{19}$ may together form —OCH$_2$O—.

In still more preferred compositions of this invention $R_1$, $R_2$, $R_3$, $R_4$, $R_5$, $R^6$, $R^7$ and $R^8$ are each independently selected from the group consisting of methyl and hydrogen; $R^9$, $R^{10}$, $R^{11}$, $R^{12}$, $R^{13}$, $R^{14}$, $R^{15}$ and $R^{16}$ are each independently selected from hydrogen and methyl or $R^9$ and $R^{10}$ may together form a carbonyl, or $R^{13}$ and $R^{14}$ may together form a carbonyl with the proviso that $R^9$, $R^{10}$, $R^{11}$, $R^{12}$, $R^{13}$, $R^{14}$, $R^{15}$ and $R^{16}$ are not all simultaneously hydrogen; $R^{17}$, $R^{18}$, $R^{19}$, $R^{20}$ and $R^{21}$ are each independently selected from the group consisting of hydrogen, halo, $CF_3$, $OR^{22}$ wherein $R^{22}$ is methyl, methyl, or $R^{17}$ and $R^{18}$ may together form —CH=CH—CH=CH—, or $R^{18}$ and $R^{19}$ may together form —OCH$_2$O—

In an even more preferred composition of this invention $R^1$ and $R^5$ are each methyl; $R_2$, $R_3$, $R_4$, $R^6$, $R^7$, $R^8$ are each hydrogen; $R^9$, $R^{10}$, $R^{11}$, $R^{12}$, $R^{13}$, $R^{14}$, $R^{15}$ and $R^{16}$ are each independently selected from hydrogen and methyl or $R^9$ and $R^{10}$ may together form a carbonyl, or $R^{13}$ and $R^{14}$ may together form a carbonyl with the proviso that $R^9$, $R^{10}$, $R^{11}$, $R^{12}$, $R^{13}$, $R^{14}$, $R^{15}$ and $R^{16}$ are not all simultaneously hydrogen; $R^{17}$, $R^{18}$, $R^{19}$, $R^{20}$ and $R^{21}$ are each independently selected from the group consisting of hydrogen, halo, methyl, $OR^{22}$ wherein $R^{22}$ is methyl, or $R^{17}$ and $R^{18}$ may together form —CH=CH—CH=CH—, or $R^{18}$ and $R^{19}$ may together form —OCH$_2$O—.

In still more preferred compositions of this invention $R^1$ and $R^5$ are each methyl; $R_2$, $R_3$, $R_4$, $R^6$, $R^7$, $R^8$ are each hydrogen; $R^9$, $R^{10}$ are selected from hydrogen, methyl, or may together form a carbonyl; $R^{11}$ and $R^{12}$ are selected from hydrogen and methyl; $R^{13}$ and $R^{14}$ are selected from hydrogen and methyl or may together form a carbonyl; $R^{15}$ and $R^{16}$ are hydrogen with the proviso that $R^9$, $R^{10}$, $R^{11}$, $R^{12}$, $R^{13}$, $R^{14}$, $R^{15}$ and $R^{16}$ are not all simultaneously hydrogen; $R^{17}$ is selected from the group consisting of hydrogen, chloro, fluoro or methoxy; $R^{18}$ and $R^{19}$ are each selected from the group consisting of hydrogen or methoxy, or $R^{18}$ and $R^{19}$ may together form —OCH$_2$O—, or $R^{17}$ and $R^{18}$ may together form —CH=CH—CH=CH—, $R^{20}$ is hydrogen; and $R^{21}$ is selected from hydrogen or chloro.

Most preferably, the substituted piperazine compounds of this invention are selected from the group consisting of N-(2,6-dimethylphenyl)-2-{4-[2-hydroxy-3-(2-methoxyphenoxy)propyl]-3-oxopiperazinyl}acetamide, N-(2,6-dimethylphenyl)-2-{4-[2-hydroxy-3-(2-methoxyphenoxy)propyl]-3,5-dimethylpiperazinyl}acetamide, 2-{(5S,2R)-4-[2-hydroxy-3-(2-methoxyphenoxy)propyl]-2,5-dimethylpiperazinyl}-N-(2,6-dimethylphenyl)acetamide, 2-{2,5-diaza-5-[2-hydroxy-3-(2-methoxyphenoxy)propyl]bicyclo[4.4.0]dec-2-yl}-N-(2,6-dimethylphenyl)acetamide, N-(2,6-dimethylphenyl)-2-{4-[2-hydroxy-3-(2-methoxyphenoxy) propyl]-3-oxopiperazinyl}acetamide, N-(2,6-dimethylphenyl)-2-{4-[2-hydroxy-3-(2-methoxyphenoxy)propyl]-3,3-dimethylpiperazinyl}acetamide, 2-{5-[(2S)-2-hydroxy-3-(2-methoxyphenoxy)propyl](1S,4S)-2,5-diazabicyclo[2.2.1]hept-2-yl}-N-(2,6-dimethylphenyl)acetamide, N-(2,6-dimethylphenyl)-2-{4-[2-hydroxy-4-(2-methoxyphenoxy)butyl]-piperazinyl}acetamide, N-(2,6-dimethylphenyl)-2-{4-[4-(4-fluorophenoxy)-2-hydroxybutyl]-piperazinyl}acetamide, 2-(4-{4-[4-(tert-butyl)phenoxy]-2-hydroxybutyl}piperazinyl)-N-(2,6-dimethylphenyl)acetamide, N-(2,6-dimethylphenyl)-2-{4-[2-hydroxy-4-(4-phenylphenoxy)butyl]piperazinyl}acetamide, N-(2,6-dimethylphenyl)-2-{4-[2-hydroxy-4-(4-methoxyphenoxy)butyl]-piperazinyl}acetamide, 2-{(3S)-4-[(2S)-3-(2-fluorophenoxy)-2-hydroxypropyl]-3-methylpiperazinyl}-N-(2,6-dimethylphenyl)acetamide, 2-{(3S)-4-[(2S)-3-(2-fluorophenoxy)-2-hydroxypropyl]-3-methylpiperazinyl}-N-(2,6-dichlorophenyl)acetamide, 2-{(3S)-4-[(2S)-3-(2-fluorophenoxy)-2-hydroxypropyl]-3-methylpiperazinyl}-N-(4-sulfamoylphenyl)acetamide, 2-{(3S)-4-[(2S)-3-(2-fluorophenoxy)-2-hydroxypropyl]-3-methylpiperazinyl}-N-(5-methoxy-3-(trifluoromethyl)phenyl]acetamide, 2-{(3S)-4-[(2S)-3-(2-fluorophenoxy)-2-hydroxypropyl]-3-methylpiperazinyl}-N-indan-5-ylacetamide, 2-{(3S)-4-[(2S)-3-(2-fluorophenoxy)-2-hydroxypropyl]-3-methylpiperazinyl}-N-naphthylacetamide, 2-{(3S)-4-[(2S)-3-(2-fluorophenoxy)-2-hydroxypropyl]-3-methylpiperazinyl}-N-(4-chloronaphthyl)acetamide, 2-{(3S)-4-[(2S)-3-(2-fluorophenoxy)-2-hydroxypropyl]-3-methylpiperazinyl}-N-(2-pyrrolylphenyl)acetamide, 2-{(3S)-4-[(2S)-3-(2-fluorophenoxy)-2-hydroxypropyl]-3-methylpiperazinyl}-N-phenylacetamide, 2-{(3S)-4-[(2S)-3-(2-fluorophenoxy)-2-hydroxypropyl]-3-methylpiperazinyl}-N-(2-chlorophenyl)acetamide, 2-{(3S)-4-[(2S)-3-(2-fluorophenoxy)-2-hydroxypropyl]-3-methylpiperazinyl}-N-(2-chloro-4-methylphenyl)acetamide, 2-{(3S)-4-[(2S)-3-(2-fluorophenoxy)-2-hydroxypropyl]-3-methylpiperazinyl}-N-[2-(1-methylvinyl)phenyl]acetamide, 2-{(3S)-4-[(2S)-3-(2-fluorophenoxy)-2-hydroxypropyl]-3-methylpiperazinyl}-N-(2-methylphenyl)acetamide, 2-{(3S)-4-[(2S)-3-(2-fluorophenoxy)-2-hydroxypropyl]-3-methylpiperazinyl}-N-[6-methyl-2-(methylethyl)phenyl]acetamide, 2-{(3S)-4-[(2S)-3-(2-fluorophenoxy)-2-hydroxypropyl]-3-methylpiperazinyl}-N-(3-methylthiophenyl)acetamide, 2-{(3S)-4-[(2S)-3-(2-fluorophenoxy)-2-hydroxypropyl]-3-methylpiperazinyl}-N-(4-chloro-2-methoxy-5-methylphenyl)acetamide, 2-{(3S)-4-[(2S)-3-(2-fluorophenoxy)-2-hydroxypropyl]-3-methylpiperazinyl}-N-[4-(dimethylamino) phenyl]acetamide, 2-{(3S)-4-[(2S)-3-(2-fluorophenoxy)-2-hydroxypropyl]-3-methylpiperazinyl}-N-(2,4-dimethoxyphenyl)acetamide, 2-{(3S)-4-[(2S)-3-(2-fluorophenoxy)-2-hydroxypropyl]-3-methylpiperazinyl}-N-(3,4-dichlorophenyl)acetamide, 2-{(3S)-4-[(2S)-3-(2-fluorophenoxy)-2-hydroxypropyl]-3-methylpiperazinyl}-N-(4-chlorophenyl)acetamide, 2-{(3S)-4-[(2S)-3-(2-fluorophenoxy)-2-hydroxypropyl]-3-methylpiperazinyl}-N-(3-chlorophenyl)acetamide, 2-{(3S)-4-[(2S)-3-(2-fluorophenoxy)-2-hydroxypropyl]-3-methylpiperazinyl}-N-(3,5-dichlorophenyl)acetamide, 2-{(3S)-4-[(2S)-3-(2-fluorophenoxy)-2-hydroxypropyl]-3-methylpiperazinyl}-N-(4-methoxyphenyl)acetamide, 2-{(3S)-4-[(2S)-3-(2-fluorophenoxy)-2-hydroxypropyl]-3-methylpiperazinyl}-N-(4-methylphenyl)acetamide, 2-{(3S)-4-[(2S)-3-(2-fluorophenoxy)-2-hydroxypropyl]-3-methylpiperazinyl}-N-(3-methylphenyl)acetamide, 2-{(3S)-4-[(2S)-3-(2-fluorophenoxy)-2-hydroxypropyl]-3-methylpiperazinyl}-N-(4-fluorophenyl)acetamide, 2-{(3S)-4-[(2S)-3-(2-fluorophenoxy)-2-hydroxypropyl]-3-methylpiperazinyl}-N-(4-cyanophenyl)acetamide, 2-{(3S)-4-[(2S)-3-(2-fluorophenoxy)-2-hydroxypropyl]-3-methylpiperazinyl}-N-(4-acetylphenyl)acetamide, 2-{(3S)-4-[(2S)-3-(2-fluorophenoxy)-2-hydroxypropyl]-3-methylpiperazinyl}-N-(2-methoxyphenyl)acetamide, 2-{(3S)-4-[(2S)-3-(2-fluorophenoxy)-2-hydroxypropyl]-3-methylpiperazinyl}-N-[4-(trifluoromethyl)phenyl]acetamide, 2-{(3S)-4-[(2S)-3-(2-fluorophenoxy)-2-hydroxypropyl]-3-methylpiperazinyl}-N-[4-chloro-3-(trifluoromethyl)phenyl]acetamide, 2-{(3S)-4-[(2S)-3-(2-fluorophenoxy)-2-hydroxypropyl]-3-methylpiperazinyl}-N-(3,5-dimethoxyphenyl)acetamide, 2-{(3S)-4-[(2S)-3-(2-fluorophenoxy)-2-hydroxypropyl]-3-methylpiperazinyl}-N-(4-morpholin-4-ylphenyl)acetamide, 2-{(3S)-4-[(2S)-3-(2-fluorophenoxy)-2-hydroxypropyl]-3-methylpiperazinyl}-N-(3-fluoro-4-methoxyphenyl)acetamide, 2-{(3S)-4-[(2S)-3-(2-fluorophenoxy)-2-hydroxypropyl]-3-methylpiperazinyl}-N-(3,4,5-trimethoxyphenyl)acetamide, 2-{(3S)-4-[(2S)-3-(2-fluorophenoxy)-2-hydroxypropyl]-3-methylpiperazinyl}-N-(3,4-dimethoxyphenyl)acetamide, 2-{(3S)-4-[(2S)-3-(2-fluorophenoxy)-2-hydroxypropyl]-3-methylpiperazinyl}-N-(4-chloro-2-fluorophenyl)acetamide, and 2-{(3S)-4-[(2S)-3-(2-fluorophenoxy)-2-hydroxypropyl]-3-methylpiperazinyl}-N-[2-(hydroxymethyl-6-methylphenyl]acetamide.

The following definitions apply to terms as used herein.

"Halo" or "Halogen"—alone or in combination means all halogens, that is, chloro (Cl), fluoro (F), bromo (Br), iodo (I).

"Hydroxyl" refers to the group —OH.

"Thiol" or "mercapto" refers to the group —SH.

"Alkyl"—alone or in combination means an alkane-derived radical containing from 1 to 20, preferably 1 to 15, carbon atoms (unless specifically defined). It is a straight chain alkyl, branched alkyl or cycloalkyl. Preferably, straight or branched alkyl groups containing from 1–15, more preferably 1 to 8, even more preferably 1–6, yet more preferably 1–4 and most preferably 1–2, carbon atoms, such as methyl, ethyl, propyl, isopropyl, butyl, t-butyl and the like. The term "lower alkyl" is used herein to describe the straight chain alkyl groups described immediately above. Preferably, cycloalkyl groups are monocyclic, bicyclic or tricyclic ring systems of 3–8, more preferably 3–6, ring members per ring, such as cyclopropyl, cyclobutyl, cyclopentyl, cyclohexyl, adamantyl and the like. Alkyl also includes a straight chain or branched alkyl group that contains or is interrupted by a cycloalkyl portion. The straight chain or branched alkyl group is attached at any available point to produce a stable compound. Examples of this include, but are not limited to, 4-(isopropyl)-cyclohexylethyl or 2-methyl-cyclopropylpentyl. A substituted alkyl is a straight chain alkyl, branched alkyl, or cycloalkyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Alkenyl"—alone or in combination means a straight, branched, or cyclic hydrocarbon containing 2–20, preferably 2–17, more preferably 2–10, even more preferably 2–8, most preferably 2 to 4 carbon atoms with at least one, preferably 1–3, more preferably 1–2, and most preferably one, carbon to carbon double bond. In the case of a cycloalkyl group, conjugation of more than one carbon to carbon double bond is not such as to confer aromaticity to the ring. Carbon to carbon double bonds may be either contained within a cycloalkyl portion, with the exception of cyclopropyl, or within a straight chain or branched portion. Examples of alkenyl groups include ethenyl, propenyl, isopropenyl, butenyl, cyclohexenyl, cyclohexenylalkyl and the like. A substituted alkenyl is the straight chain alkenyl, branched alkenyl or cycloalkenyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxy, alkoxycarbonyl, aryloxycarbonyl, heteroaryloxycarbonyl, or the like attached at any available point to produce a stable compound.

"Alkynyl"—alone or in combination means a straight or branched hydrocarbon containing 2–20, preferably 2–17, more preferably 2–10, even more preferably 2–8, most preferably 2–4, carbon atoms containing at least one, preferably one, carbon to carbon triple bond. Examples of alkynyl groups include ethynyl, propynyl, butynyl and the like.

A substituted alkynyl refers to the straight chain alkynyl or branched alkynyl defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like attached at any available point to produce a stable compound.

"Alkyl alkenyl" refers to a group —R—CR'=CR'"R"', where R is lower alkyl, or substituted lower alkyl, R', R''', R" may independently be hydrogen, halogen, lower alkyl, substituted lower alkyl, acyl, aryl, substituted aryl, hetaryl, or substituted hetaryl as defined below.

"Alkyl alkynyl" refers to a groups —RC≡CR' where R is lower alkyl or substituted lower alkyl, R' is hydrogen, lower alkyl, substituted lower alkyl, acyl, aryl, substituted aryl, hetaryl, or substituted hetaryl as defined below.

"Alkoxy" denotes the group —OR, where R is lower alkyl, substituted lower alkyl, acyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined.

"Alkylthio" denotes the group —SR, —S(O)$_{n=1-2}$—R, where R is lower alkyl, substituted lower alkyl, aryl, substituted aryl, aralkyl or substituted aralkyl as defined herein.

"Acyl" denotes groups —C(O)R, where R is hydrogen, lower alkyl substituted lower alkyl, aryl, substituted aryl and the like as defined herein.

"Aryloxy" denotes groups —OAr, where Ar is an aryl, substituted aryl, heteroaryl, or substituted heteroaryl group as defined herein.

"Amino" denotes the group NRR', where R and R' may independently by hydrogen, lower alkyl, substituted lower alkyl, aryl, substituted aryl, hetaryl, or substituted hetaryl as defined herein or acyl.

"Amido" denotes the group —C(O)NRR', where R and R' may independently by hydrogen, lower alkyl, substituted lower alkyl, aryl, substituted aryl, hetaryl, substituted hetaryl as defined herein.

"Carboxyl" denotes the group —C(O)OR, where R is hydrogen, lower alkyl, substituted lower alkyl, aryl, substituted aryl, hetaryl, and substituted hetaryl as defined herein.

"Aryl"—alone or in combination means phenyl or naphthyl optionally carbocyclic fused with a cycloalkyl of preferably 5–7, more preferably 5–6, ring members and/or optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Substituted aryl" refers to aryl optionally substituted with one or more functional groups, e.g., halogen, lower alkyl lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heterocycle" refers to a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl or benzo[b]thienyl) and having at least one hetero atom, such as N, O or S, within the ring, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heteroaryl"—alone or in combination means a monocyclic aromatic ring structure containing 5 or 6 ring atoms, or a bicyclic aromatic group having 8 to 10 atoms, containing one or more, preferably 1–4, more preferably 1–3, even more preferably 1–2, heteroatoms independently selected from the group O, S, and N, and optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. Examples of heteroaryl groups are pyridinyl, pyridazinyl, pyrazinyl, quinazolinyl, purinyl, quinolinyl, isoquinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl, benzothiazolyl, benzoxazolyl, and the like. A substituted heteroaryl contains a substituent attached at an available carbon or nitrogen to produce a stable compound.

"Heterocyclyl"—alone or in combination means a non-aromatic cycloalkyl group having from 5 to 10 atoms in which from 1 to 3 carbon atoms in the ring are replaced by heteroatoms of O, S or N, and are optionally benzo fused or fused heteroaryl of 5–6 ring members and/or are optionally substituted as in the case of cycloalkyl. Heterocycyl is also intended to include oxidized S or N, such as sulfinyl, sulfonyl and N-oxide of a tertiary ring nitrogen. The point of attachment is at a carbon or nitrogen atom. Examples of heterocyclyl groups are tetrahydrofuranyl, dihydropyridinyl, piperidinyl, pyrrolidinyl, piperazinyl, dihydrobenzofuryl, dihydroindolyl, and the like. A substituted hetercyclyl contains a substituent nitrogen attached at an available carbon or nitrogen to produce a stable compound.

"Substituted heteroaryl" refers to a heterocycle optionally mono or poly substituted with one or more functional groups, e.g., halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Aralkyl" refers to the group —R—Ar where Ar is an aryl group and R is lower alkyl or substituted lower alkyl group. Aryl groups can optionally be unsubstituted or substituted with, e.g., halogen, lower alkyl, alkoxy, alkylthio, acetylene, amino, amido, carboxyl, hydroxyl, aryl, aryloxy, heterocycle, substituted heterocycle, hetaryl, substituted betaryl, nitro, cyano, thiol, sulfamido and the like.

"Heteroarylalkyl" refers to the group —R-HetAr where HetAr is an heteroaryl group and R lower alkyl or substituted lower alkyl. Heteroarylalkyl groups can optionally be unsubstituted or substituted with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloalkyl" refers to a divalent cyclic or polycyclic alkyl group containing 3 to 15 carbon atoms.

"Substituted cycloalkyl" refers to a cycloalkyl group comprising one or more substituents with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Alkyl cycloalkyl" denotes the group —R-cycloalkyl where cycloalkyl is a cycloalkyl group and R is a lower alkyl or substituted lower alkyl. Cycloalkyl groups can optionally be unsubstituted or substituted with e.g. halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Optional" and "optionally" mean that the subsequently described event or circumstance may or may not occur, and that the description includes instances where the event or circumstance occurs and instances in which it does not. For example, "optional pharmaceutical excipients" indicates that a formulation so described may or may not include pharmaceutical excipients other than those specifically stated to be present, and that the formulation so described includes instances in which the optional excipients are present and instances in which they are not.

"Treating" and "treatment" refer to any treatment of a disease in a mammal, particularly a human, and include:
(i) preventing the disease from occurring in a subject which may be predisposed to the disease but has not yet been diagnosed as having it;
(ii) inhibiting the disease, i.e., arresting its development; or
(iii) relieving the disease, i.e., causing regression of the disease.

The compositions of this invention are useful for treating mammals in a therapy selected from the group consisting of protecting skeletal muscles against damage resulting from trauma, protecting skeletal muscles subsequent to muscle or systemic diseases such as intermittent claudication, to treat shock conditions, to preserve donor tissue and organs used in transplants, and to treat cardiovascular diseases including atrial and ventricular arrhythmias, Prinzmetal's (variant) angina, stable angina, and exercise induced angina, congestive heart disease, and myocardial infarction. The treatment is accomplished using a therapeutically effective amount of at least one compound of this invention and/or a pharmaceutically acceptable acid addition salt thereof in admixture with a pharmaceutically acceptable excipient.

Compounds falling within the scope of this invention include the optical isomers (+) and (−) and R- and S-isomers of the above-identified compounds and mixtures thereof. This invention includes the individual isomers and all possible mixtures thereof.

All of the aforementioned embodiments include the pharmaceutically acceptable acid addition salts thereof, particularly the mono- and dihydrochlorides, and mixtures thereof.

The compounds having the general formula I can be prepared as outlined in Schemes 1–5. A general synthesis of the compounds of this invention is outlined in Scheme 1. Compound IV can be prepared by N-acylation of substituted aniline II with 2-substituted chloroacetylchloride III. Compound II is available commercially or readily prepared through reduction of the corresponding nitrobenzene derivative (acid/$SnCl_2$ or catalytic hydrogenation, see Advanced Organic Chemistry, Ed. J. March, (1992) A. Wiley-Interscience). Some examples of commercially available substituted anilines corresponding to general structure II include 2,6-dimethylaniline, 2,3-dimethylaniline, 2-methylaniline, 4-methylaniline, 4-methylaniline, 2,4-dichloroaniline, 3,4-dichloroaniline, 2,5-dichloroaniline, 2,4-dichloroaniline, 2-chloroaniline, 3-chloroaniline, 2,6-difluoroaniline, 2,5-difluoroaniline, 3,4-difluoroaniline, 2-fluoroaniline, 4-fluoroaniline, 3-fluoroaniline, 2-fluoro-6-chloroaniline, 4-fluoro-3-chloroaniline.

SCHEME 1

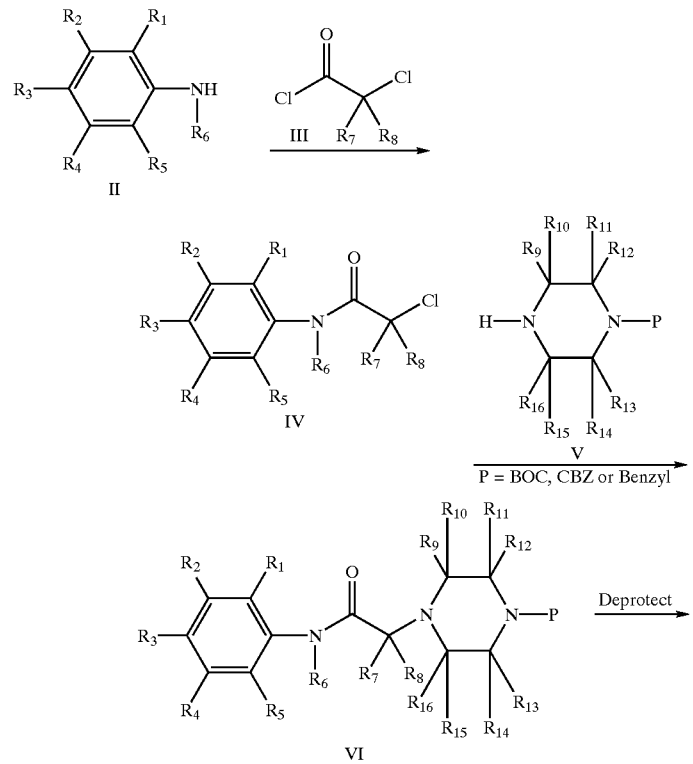

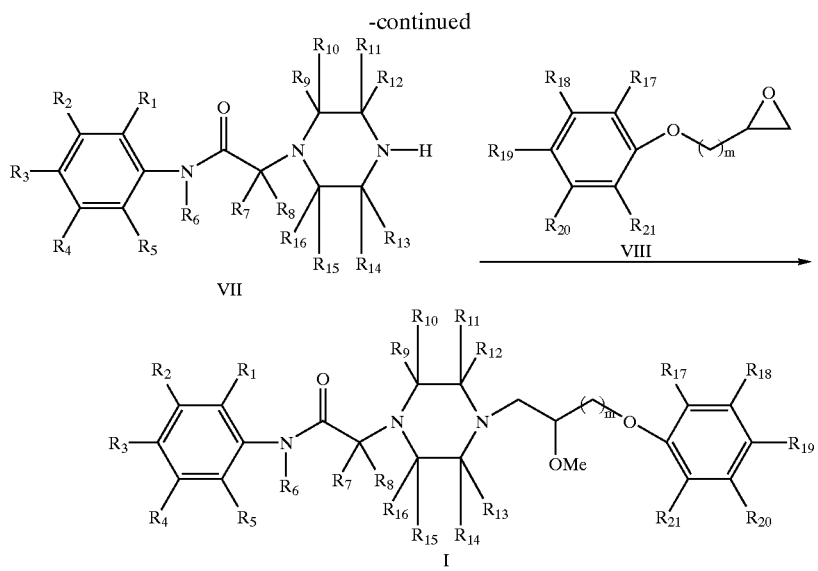

Compound VI can be obtained by reacting compound IV with N-protected substituted piperazine V through warming in an appropriate solvent (e.g. DMF, EtOH). Protection of the nitrogen of compound V is only required when it is useful to control the regiochemistry of the addition of Compound V with compound IV. In some cases, compound V can be obtained from commercial resources. Examples of commercially available compounds corresponding to general structure V include 2-methyl piperazine, 2,5-dimethyl piprazine and 2,6-dimethyl piperazine. Deprotection of compound VI can be accomplished using the standard conditions (e.g. for Boc group use TFA, for CBZ and benzyl use hydrogenation). Compound I can be prepared by reacting compound VII with epoxide VIII through warming in an appropriate solvent (ethanol, DMF).

SCHEME 2

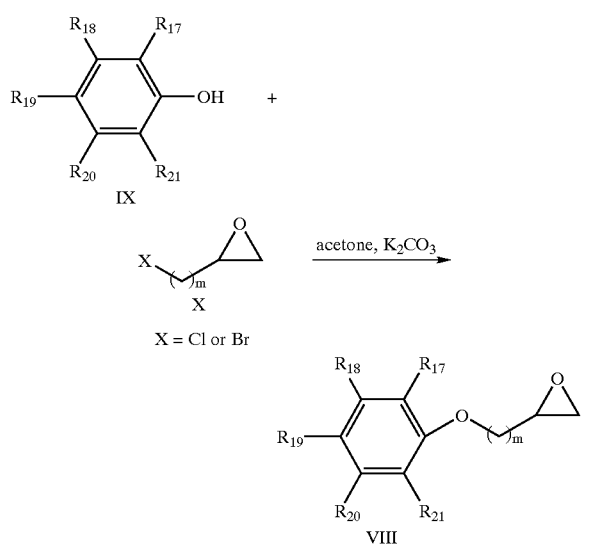

$X = Cl$ or $Br$

Epoxide VIII (where m=1 or 2) can be prepared as outlined in Scheme 2. Heating substituted phenol IX with epichlorohydrin, epibromohydrin, or 4-bromo-1,2-epoxybutane and potassium carbonate in acetone can afford epoxide VIII. Compound IX can be obtained from commercial resources. Example of commercially available compounds of compounds XI include 2-chlorophenol, 2-fluorophenol, 2-methoxyphenol, 2-methylphenol, sesamol, 2,6-dichlorophenol, 3,5-dichlorophenol, 2,6-difluorophenol, 2,4-difluorophenol-5-indanol, 3-chloro-4-fluorophenol, 2,chloro-4-fluorophenol and 5,6,7,8-tetrahydro-2-naphthol. In some cases compound VIII can be obtained from commercial sources. Examples of commercially available compounds corresponding to general structure VIII include benzyl glycidyl ether, glycidyl 2-methylphenyl ether, glycidyl 4-methoxyphenyl ether, glycidyl 4-chlorophenyl ether, glycidyl 2-chlorophenyl ether, glycidyl 2-methoxyphenyl ether, glycidyl 4-methylphenyl ether, glycidyl 3,4-dichlorophenyl ether and glycidyl 4-fluorophenyl ether.

SCHEME 3

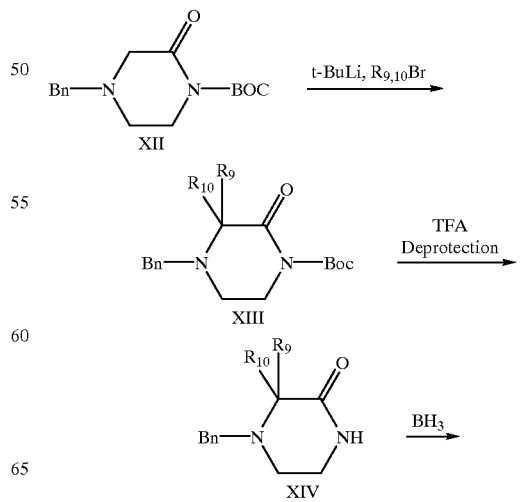

-continued

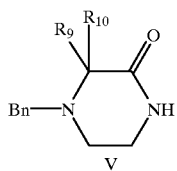

Compound V can be prepared as described in Scheme 3. Alkylation of compound XII with alkyl halides using t-BuLi as base can afford compound XIII as described by Pohlman et. al. (J. Org. Chem, (1997), 62, 1016–1022). Reduction of XI using diborane can afford N-benzyl protected version of compound V after N-Boc deprotection with trifluoroacetic acid (TFA) [for the diborane reduction see Jacobson et. al., J. Med. Chem, (1999), 42, 1123–1144].

SCHEME 4

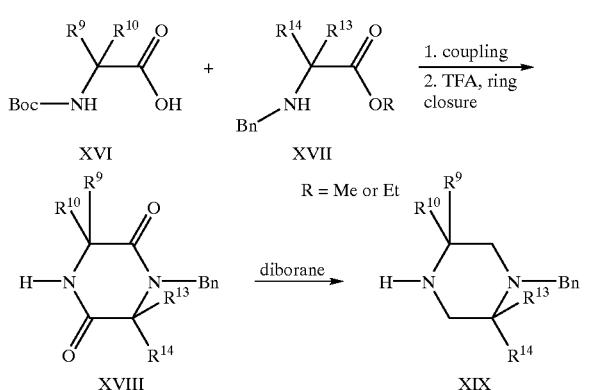

Compound V can also be prepared through standard coupling (e.g. EDC or PyBroP) of D or L amino acids and standard deprotection as outlined in Scheme 4 [For preparations of diketopiperazines see—P. Cledera et al. Tetrahedron, (1998) p. 12349–12360 and R. A. Smith et al Bioorg. Med. Chem. Lett. (1998) p. 2369–2374]. Reduction of the diketopiperazine with diborane can afford compound XIX the N-benzyl protected version of compound V. Compound V also includes the bicyclic homologs of piperazine (1S,4S)-(+)-2,5-diazabicyclo[2.2.1]heptane 83, 3,8-diazabicyclo[3.2.1]octane 84, and 2,5-diazabicyclo[2.2.2]octane 85.

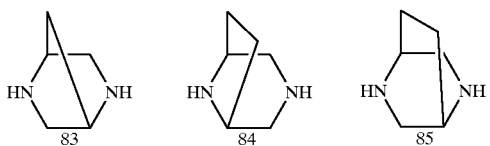

Commercially available bicyclic analogs include (1S,4S)-(+)-2,5-diazabicyclo[2.2.1]heptane 83. Compounds 84, 85, and the (1R,4R) isomer of 83 can be prepared by published procedures (for 84 and 85—see Sturm, P. A. et. al., J. Med. Chem. 1974, 17, 481–487; for 83 see—Barish, T. F. and Fox, D. E. J. Org. Chem., 1990, 55, 1684–1687).

A specific example of the preparation of a compound from this invention is disclosed in Schemes 5, 6 and 7 to further illustrate how to prepare the compounds of this invention. In particular, 2,6-dichloroaniline was acylated with 2-chloroacetyl chloride 2 using saturated bicarbonate and ether (1:1) as base and co-solvent, respectively to afford the chloroacetamide derivative 3. Further reaction of compound 3 with 2,6-dimethyl piperazine afforded compound 5 through warming in ethanol. Reaction of compound 5 with epoxide 6 by warming both components in ethanol at reflux afforded 2,6-dimethyl piperazine derivative 7. Compound 6 in turn was prepared by warming epichlorohydrin with 2-methoxyphenol in acetone in the presence of $K_2CO_3$ as described in Scheme 6.

SCHEME 5

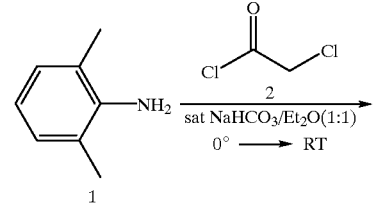

SCHEME 6

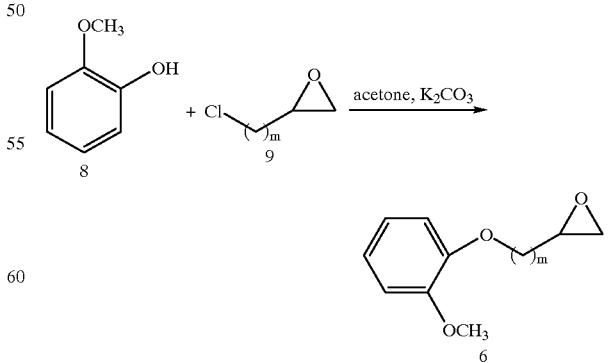

6a. m = 1
6b. m = 2

A specific synthesis of compound 14 is described in Scheme 7. Compound 11 was prepared by opening of epoxide 6 with Boc-ethylenediamine through warming in EtOH. Acylation of compound 11 was accomplished using chloroacetyl chloride in dichloromethane using diisopropylethyl amine as a base. Removal of the Boc group using TFA followed by ring closure through warming in EtOH afforded compound 13. Reaction of compound 13 with 6 as described above afforded compound 14.

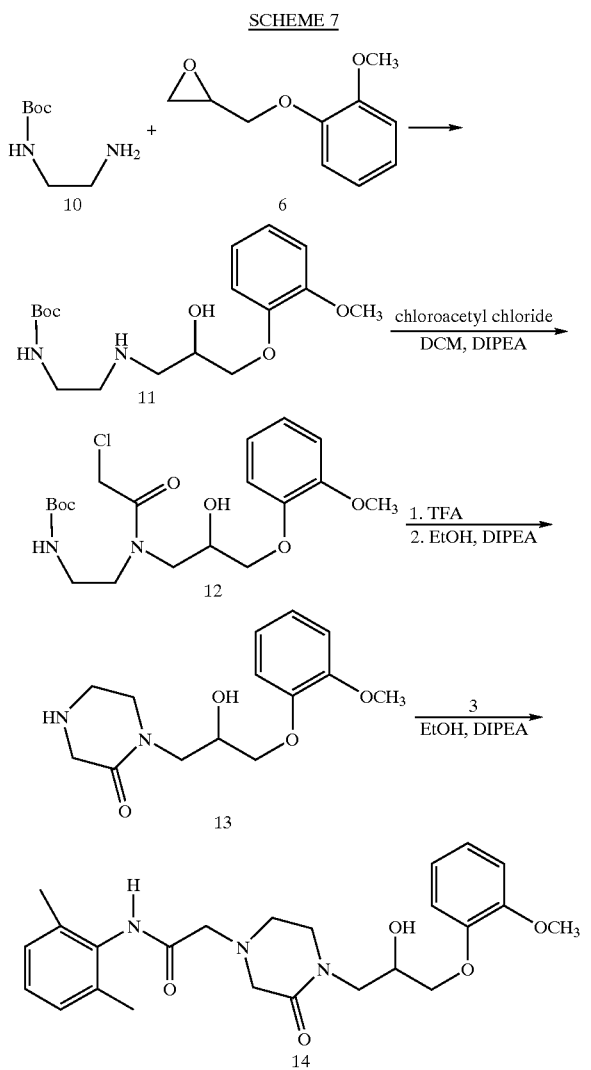

SCHEME 7

The acid addition salts of the compounds of this invention may be converted to the corresponding free base by treating with a suitable base, such as potassium carbonate or sodium hydroxide, typically in the presence of aqueous solvent, and at a temperature of between about 0 degrees C and 100 degrees C. The free base form is isolated by conventional means, such as extraction with an organic solvent.

Salts of the compounds of this invention may be interchanged by taking advantage of differential solubilities and volatilities, or by treating with the appropriately loaded ion exchange resin. This conversion is carried out at a temperature between about 0° C. and the boiling point of the solvent being used as the medium for the procedure. Administration of the active compounds and salts described herein can be via any of the accepted modes of administration for therapeutic agents. These methods include oral, parenteral, transdermal, subcutaneous and other systemic modes. The preferred method of administration is oral, except in those cases where the subject is unable to ingest, by himself, any medication. In those instances it may be necessary to administer the composition parenterally.

Depending on the intended mode, the compositions may be in the form of solid, semi-solid or liquid dosage forms, such as, for example, tablets, suppositories, pills, capsules, powders, liquids, suspensions, or the like, preferably in unit dosage forms suitable for single administration of precise dosages. The compositions may include one or more conventional pharmaceutical excipients and at least one active compound of this invention or the pharmaceutically acceptable salts thereof and, in addition, may include other medicinal agents, pharmaceutical agents, carriers, adjuvants, diluents, etc.

The amount of active compound administered will, of course, be dependent on the subject being treated, the subject's weight, the severity of the affliction, the manner of administration and the judgment of the prescribing physician. However, an effective dosage is in the range of 0.1–30 mg/kg/day, preferably 0.5–20 mg/kg/day. For an average 70 kg human, this would amount to 7–2100 mg per day, or preferably 35–1400 mg/day. Since many of the effects of the compounds herein (protect skeletal muscles against damage resulting from trauma; protect skeletal muscles subsequent to muscle or systemic diseases such as intermittent claudication; treat shock conditions; preserve donor tissue and organs used in transplants; and treat cardiovascular diseases including atrial and ventricular arrhythmias, Prinzmetal's (variant) angina, stable angina, exercise induced angina, congestive heart disease, and myocardial infarction) are achieved through a similar mechanism (partial fatty acid oxidation inhibition) dosages (and forms of administration) are all generally within the same general and preferred ranges for all these utilities.

For solid compositions, conventional non-toxic solid include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administrable compositions can, for example, be prepared by dissolving, dispersing, etc. an active compound as defined above and optional pharmaceutical adjuvants in a excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound(s), a therapeutically effective amount, i.e. in an amount effective to alleviate the symptoms of the subject being treated. For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 10%–95% active ingredient, preferably 1–70%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795, which is incorporated herein by reference. In another recent approach, the compositions of this invention can be administered orally in a sustained release dosage form using the compositions and/or methods disclosed in U.S. patent application Ser. No. 09/321,522, filed on May 27, 1999, the specification of which is incorporated herein by reference.

It is within the scope of this invention to administer one or more compounds of this invention to a mammal, and preferably to a human by other known routes of pharmaceutical dosage form administration including, but not limited to by bolus, intravenously, transdermally, through inhalation, sub-cutaneously, or any other therapeutic agent administration method or route know to one skilled in the art.

The following Examples are representative of the invention, but are not to be construed as limiting the scope of the claims.

EXAMPLE 1

N-(2,6-dimethylphenyl)-2-{4-[2-hydroxy-3-(2-methoxy)propyl]-3,5-dimethylpiperazinyl} acetamide (7)

7

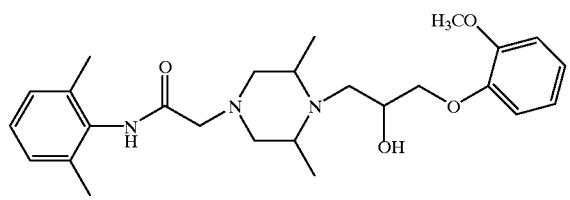

Part A
Synthesis of N-(2,6-dimethylphenyl)-2-chloroacetamide (3)
2,6-dimethylaniline (9.8 g, 81.2 mmol) was dissolved in ether (100 mL) and saturated aqueous $NaHCO_3$ (100 mL) and the reaction mixture was cooled in an ice/water bath. To the cold solution was added chloroacetyl chloride 2 (9.17 g, 81.2 mmol) dropwise over a period of 2 h. The mixture was allowed to warm to RT over 14 h. The mixture was extracted with EtOAc (3×50). The combined organic layers were dried over $MgSO_4$, filtered and concentrated. The residue was triturated in ether and filtered to afford compound 3 as a white solid.

Part B
Synthesis of N-(2,6-dimethylphenyl)-2-(3,5-dimethylpiperazinyl)acetamide (5)
To a solution of compound 3 (5 g, 25.2 mmol) in ethanol (100 mL) was added 2,6-dimethylpiperazine 4 (2.1 g, 25.0 mmol) and N,N-diisopropylamine (3.2 g, 25.2 mmol). The reaction mixture was refluxed for 24 h. The mixture was concentrated in vacuo and the residue was purified by column chromatography (10:1, DCM:MeOH) to afford compound 5.

Part C
Synthesis of glycidyl 4-methoxyphenyl ether (6)
2-methoxyphenol (1.0 g, 8.0 mmol) and epichlorohydrin (3.7 g, 40.0 mmol) were dissolved in acetone (20 mL). $K_2CO_3$ (2.2 g, 16.0 mmol) was added and the mixture was heated at 70° C. for 24 h. The reaction mixture was concentrated in vacuo. The residue was dissolved 100 mL of EtOAc, washed with 100 mL water, dried over $MgSO_4$ and filtered. The mixture was evaporated to dryness and the residue was purified using column chromatography (2:1, hexane:ethyl acetate) to afford compound 6.

Part D
Synthesis of N-(2,6-dimethylphenyl)-2-{4-[2-hydroxy-3-(2-methoxy)propyl]-3,5-dimethylpiperazinyl} acetamide (7)
To a solution of compound 5 in 10 mL EtOH (0.4 g, 1.4 mmol) was added compound 6 (0.27 g, 1.5 mmol). The reaction mixture was refluxed for 24 h. The mixture was concentrated in vacuo and the residue was purified by using Prep. TLC (10:1, DCM:MeOH) to afford compound 7.

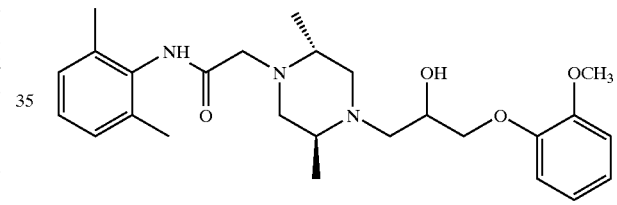

2-{(5S,2R)-4-[2-hydroxy-3-(2-methoxyphenoxy)propyl]-2,5-dimethylpiperazinyl}-N-(2,6-dimethylphenyl)acetamide (15)

Compound 15 was prepared in the manner of compound 7 substituting (2R, 5S)-dimethylpiperazine for 2,6-dimethylpiperazine 4 in part B to afford compound 15: Mass spectrum (M+1)=456.4.

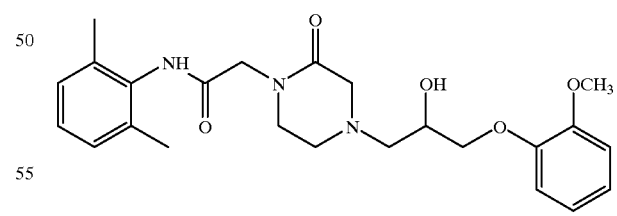

N-(2,6-dimethylphenyl)-2-{4-[2-hydroxy-3-(2-methoxyphenoxy)propyl]-2-oxopiperazinyl}acetamide (16)

Compound 16 was prepared substituting 4-benzyloxycarbonyl-2-oxo-piperazine for 2,6-dimethylpiperazine 4 in part B of compound 7 that was carried on to the final target in the manner of compound 7 after removal of the CBZ protecting group (hydrogenation—20 psi, 10% palladium on carbon) to afford compound 16: Mass spectrum (M+1)=442.41.

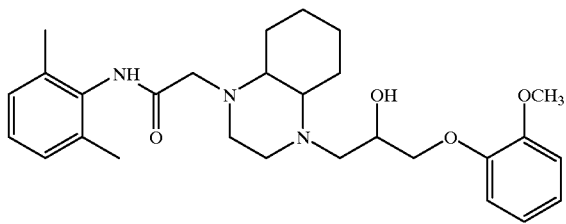

2,5-diaza-5-[2-hydroxy-3-(2-methoxyphenoxy)propyl]bicyclo[4.4.0]dec-2-yl}-N-(2,6-dimethylphenyl)acetamide (17)

Compound 17 was prepared in the manner of compound 7 substituting 15 perhydroquinoxaline for 2,6-dimethylpiperazine 4 in part B to afford compound 15: Mass spectrum (M+1)=482.4.

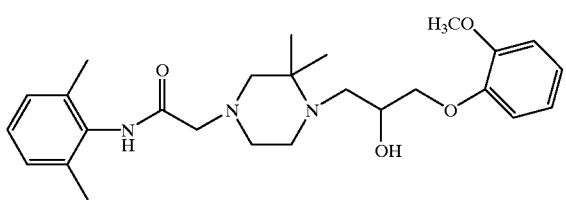

N-(2,6-dimethylphenyl)-2-{4-[2-hydroxy-3-(2-methoxyphenoxy)propyl]-3,3-dimethylpiperazinyl}acetamide (18)

Compound 18 was prepared in the manner of compound 7 substituting 2,2-dimethylpiperazine for 2,6-dimethylpiperazine 4 in part B to afford compound 18: Mass spectrum (M+1)=456.51

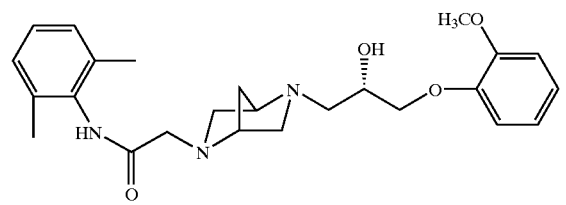

2-{5-[(2S)-2-hydroxy-3-(2-methoxyphenoxy)propyl](1S,4S)-2,5-diazabicyclo[2.2.1]hept-2-yl}-N-(2,6-dimethylphenyl)acetamide (19)

Compound 19 was prepared in the manner of compound 7 substituting (1S,4S)-(+)-2,5-Diazabicyclo[2.2.1]heptane for 2,6-dimethylpiperazine 4 in part B to afford compound 19: Mass spectrum (M+1)=481.5

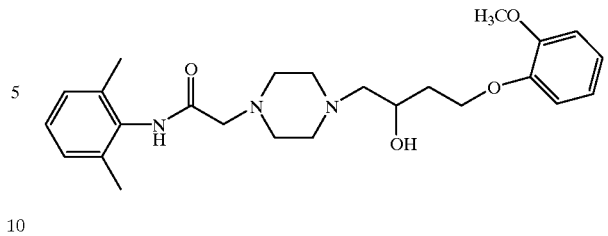

N-(2,6-dimethylphenyl)-2-{4-[2-hydroxy-4-(2-methoxyphenoxy)butyl]-piperazinyl}acetamide (20)

Compound 20 was prepared in the manner of compound 7 substituting 4-bromo-1,2-epoxybutane 6b for epichlorohydrin 6a in part B to afford compound 20: Mass spectrum (M+1)=442.37

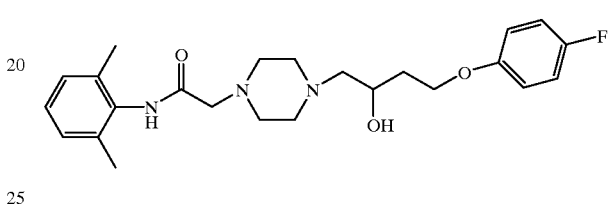

N-(2,6-dimethylphenyl)-2-{4-[4-(4-fluorophenoxy)-2-hydroxybutyl]-piperazinyl}acetamide (21) Compound 21 was prepared in the manner of compound 7 substituting 4-bromo-1,2-epoxybutane 6b for epichlorohydrin 6a in part B to afford compound 21: Mass spectrum (M+1) 430.35

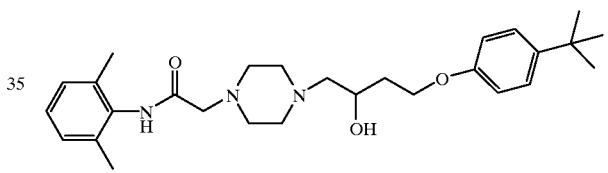

2-(4-{4-[4-(tert-butyl)phenoxyl-2-hydroxybutyl]piperazinyl)-N-(2,6-dimethylphenyl)acetamide (22)

Compound 22 was prepared in the manner of compound 7 substituting 4-bromo-1,2-epoxybutane 6b for epichlorohydrin 6a in part B to afford compound 22: Mass spectrum (M+1)=468.32

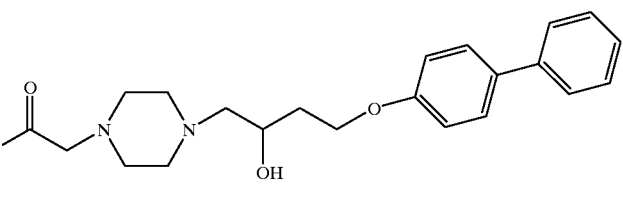

N-(2,6-dimethylphenyl)-2-{4-[2-hydroxy-4-(4-phenylphenoxy)butyl]piperazinyl}acetamide (23)

Compound 23 was prepared in the manner of compound 7 substituting 4-bromo-1,2-epoxybutane 6b for epichlorohydrin 6a in part B to afford compound 23: Mass spectrum (M+1)=488.41

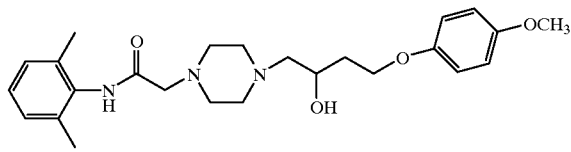

N-(2,6-dimethylphenyl)-2-{4-[2-hydroxy-4-(4-methoxyphenoxy)butyl]-piperazinyl}acetamide (24)

Compound 24 was prepared in the manner of compound 7 substituting 4-bromo-1,2-epoxybutane 6b for epichlorohydrin 6a in part B to afford compound 24: Mass spectrum (M+1)=442.37

EXAMPLE 2

N-(2,6-dimethylphenyl)-2-{4-[2-hydroxy-3-(2-methoxyphenoxy)propyl]-3-oxopiperazinyl}acetamide (14)

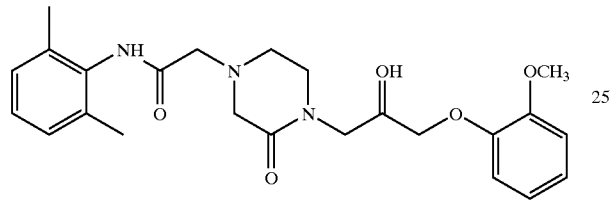

Part E
Synthesis of (tert-butoxy)-N-(2-{[2-hydroxy-3-(2-methoxyphenoxy)propyl]amino}ethyl)carboxamide (11)

Epoxide 6 (1.0 g, 5.5 mmol) and Boc-ethylenediamine (0.88 g, 5.5 mmol) were dissolved in 20 mL EtOH and the mixture was heated at reflux for 24 h. The solvent was evaporated and the residue was purified using column chromatography (1:1, Hex:EtOAc) to afford compound 11.
Synthesis of N-{2-[(tert-butoxy)carbonylamino]ethyl}-2-chloro-N[2-hydroxy-3-(2-methoxyphenoxy)propyl] acetamide (12)

Compound 11 (1.0 g, 3.0 mmol) was dissolved in 20 mL DCM and treated with diisopropylethyl amine (0.76 g, 4.5 mmol). The mixture was cooled to ° C. To the cold mixture was added dropwise chloroacetyl chloride in 5 mL DCM. The reaction mixture was allowed to stir at RT for 24 h. The mixture was diluted with 50 mL DCM and washed with 50 mL of water and 10% citric acid. The organic layer was dried over $MgSO_4$ and filtered. The solvent was evaporated under reduced pressure and the residue was crystallized from ethylether to afford compound 12.

Synthesis of 1-[2-hydroxy-3-(2-methoxyphenoxy)propyl]piperazin-2-one (13). Compound 12 (0.5 g, 1.5 mmol) was dissolved in 10 mL TFA. The mixture was allowed to stir at RT for 2 h. TFA was removed under reduced pressure. The residue was dissolved in 20 mL EtOH and treated with diisopropylethyl amine (0.76 g, 4.5 mmol). The mixture was heated at reflux for 24 h. The solvent was removed under reduced pressure to afford compound 13 which was used without further purification.
Part F
Synthesis of N-(2,6-dimethylphenyl)-2-{4-[2-hydroxy-3-(2-methoxyphenoxy)propyl]-3-oxopiperazinyl}acetamide (14)

To a solution of compound 13 in 10 mL EtOH (0.1 g, 0.30 mmol) was added compound 3 (0.7 g, 0.36 mmol) and diisopropylethyl amine (0.76 g, 0.36 mmol). The reaction mixture was heated at reflux for 24 h. The mixture was concentrated in vacuo and the residue was purified by using Prep. TLC (10:1, DCM:MeOH) to afford compound 14: Mass spectrum (M+1)=442.34

EXAMPLE 3

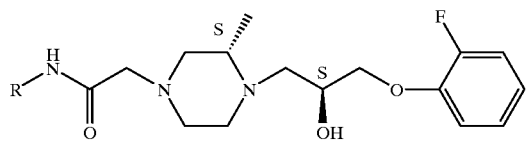

The compounds listed in Table 1, below were made in the manner of compound 14 of Example 2.

TABLE 1

|    | R                                   | MH+   |
|----|-------------------------------------|-------|
| 25 | 2,6-dimethylphenyl                  | 430.3 |
| 26 | 2,6-dichlorophenyl                  | 471   |
| 27 | 4-aminosulfonylphenyl               | 481.2 |
| 28 | 3-trifluoromethyl-5methoxyphenyl    | 500.2 |
| 29 | 5-indanyl                           | 442.2 |
| 30 | 1-naphthyl                          | 452.3 |
| 31 | 1-(4-chloronaphthyl)                | 486.3 |
| 32 | 2-N-pyrrolyl-phenyl                 | 467.3 |
| 33 | Phenyl                              | 402.2 |
| 34 | 2-chlorophenyl                      | 436.2 |
| 35 | 2-chloro-4-methylphenyl             | 450.2 |
| 36 | 2-(1-methylethenyl)phenyl           | 442.3 |
| 37 | 2-methylphenyl                      | 416.2 |
| 38 | 2-isopropyl-6-methylphenyl          | 458.4 |
| 39 | 3-methylthiophenyl                  | 448.2 |
| 40 | 2-methoxy-4-chloro-5-methylphenyl   | 480.2 |
| 41 | 4-dimethylaminophenyl               | 445.3 |
| 42 | 2,4-dimethoxyphenyl                 | 462.3 |
| 43 | 3,4-dichlorophenyl                  | 471.1 |
| 44 | 4-chlorophenyl                      | 436.3 |
| 45 | 3-chlorophenyl                      | 436.2 |
| 46 | 3,5-dichlorophenyl                  | 471.1 |
| 47 | 4-methoxyphenyl                     | 432.3 |
| 48 | 4-methylphenyl                      | 416.2 |
| 49 | 3-methylphenyl                      | 416.2 |
| 50 | 4-fluorophenyl                      | 420.2 |
| 51 | 4-cyanophenyl                       | 427.3 |
| 52 | 4-acetylphenyl                      | 444   |
| 53 | 2-methoxyphenyl                     | 432.4 |
| 54 | 4-trifluoromethylphenyl             | 470.2 |
| 55 | 3-trifluoromethyl-4-chlorophenyl    | 504.1 |
| 56 | 3,5-dimethoxyphenyl                 | 462.3 |
| 57 | 4-N-morpholinylphenyl               | 487.4 |
| 58 | 3-fluoro-4-methoxyphenyl            | 450.2 |
| 59 | 3,4,5-trimethoxyphenyl              | 492.3 |
| 60 | 3,4-dimethoxyphenyl                 | 490   |
| 61 | 2-fluoro-4-chlorophenyl             | 454.2 |
| 62 | 2-hydroxymethyl-6-methylphenyl      | 446   |

EXAMPLE 4

Compounds of this invention were evaluated in a rat heart mitochondiral assay as set forth below.
Mitochondrial Assays Rat heart mitochondria were isolated by the method of Nedergard and Cannon (methods in Enzymol. 55, 3, 1979).

Palmitoyl CoA oxidation—The Palmityl CoA oxidation was carried out in a total volume of 100 micro liters containing the following agents: 110 mM KCl, 33 mM Tris buffer at pH 8, 2 mM KPi, 2 mM $MgCl_2$, 0.1 mM EDTA, 14.7 microM defatted BSA, 0.5 mM malic acid, 13 mM carnitine, 1 mM ADP, 52 micrograms of mitochondrial protein, and 16 microM 1-C14 palmitoyl CoA (Sp. Activity 60 mCi/mmole; 20 microCi/ml, using 5 microliters per assay). The compounds of this invention were added in a DMSO solution at the following concentrations: 100 microM, 30 microM, and 3 microM. In each assay, a DMSO control was used. After 15 min at 30° C., the enzymatic reaction was centrifuged (20,000 g for 1 min), and 70 microliters of the supernatant was added to an activated reverse phase silicic acid column (approximately 0.5 ml of silicic acid). The column was eluted with 2 ml of water, and 0.5 ml of the eluent was used for scintillation counting to determine the amount of $C^{14}$ trapped as $C^{14}$ bicarbonate ion. The assay results are reported in Table 2, below.

TABLE 2

Inhibition of mitochondrial fatty acid oxidation using palmitoyl CoA as substrate - % of Control at 3 concentrations.

| Compound # | 100 μM | 30 μM | 3 μM |
|---|---|---|---|
| Ranolazine | 75% | 90% | — |
| 14 | — | — | — |
| 7 | 85% | 98% | 107% |
| 15 | 78% | 97% | 103% |
| 17 | 89% | 98% | 100% |
| 16 | 100% | 96% | — |
| 18 | 80% | | |
| 19 | 80% | | |
| 20 | — | | |
| 21 | 87% | | |
| 22 | 16% | | |
| 23 | — | | |
| 24 | — | | |
| 25 | 77% | | |
| 26 | 0% | | |
| 27 | — | | |
| 28 | 59% | | |
| 29 | 51% | | |
| 30 | 16% | | |
| 31 | 87% | | |
| 32 | 74% | | |
| 33 | 63% | | |
| 34 | 48% | | |
| 35 | 45% | | |
| 36 | 61% | | |
| 37 | 55% | | |
| 38 | 78% | | |
| 39 | 60% | | |
| 40 | 23% | | |
| 41 | 64% | | |
| 42 | 68% | | |
| 43 | 19% | | |
| 44 | 81% | | |
| 45 | 58% | | |
| 46 | 7% | | |
| 47 | 80% | | |
| 48 | 61% | | |
| 48 | 61% | | |
| 49 | 66% | | |
| 50 | 80% | | |
| 51 | 99% | | |
| 52 | — | | |
| 53 | 81% | | |
| 54 | 75% | | |
| 55 | 11% | | |
| 56 | 83% | | |
| 57 | 73% | | |
| 58 | 81% | | |
| 59 | 76% | | |
| 60 | 81% | | |
| 61 | 65% | | |
| 62 | 66% | | |

EXAMPLE 5
Palmiotoyl Carnitine Oxidation

The Palmitoyl carnitine oxidation was carried out in a total volume of 100 microliters containing the following agents: 110 mM KCl, 33 mM Tris buffer at pH 8, 2 mM KPi, 2 mM $MgCl_2$, 0.1 mM EDTA, 0.1 mg/ml of defatted BSA, 0.5 mM malic acid, 3 mM ADP, 52 micrograms of mitochondrial protein, and 43 microM 1-C14 palmitoyl carnitine (Sp. Activity 60 mCi/mmole; 20 microCi/ml, using 5 microliters per assay). The compounds of this invention were added in a DMSO solution at the following concentrations: 100 microM, 30 microM, and 3 microM. In each assay, a DMSO control was used. After 15 min at 30° C., the enzymatic reaction was centrifuged (20,000 g for 1 min), and 70 microliters of the supernatant was added to an activated reverse phase silicic acid column (approximately 0.5 ml of silicic acid). The column was eluted with 2 ml of water, and 0.5 ml of the eluent was used for scintillation counting to determine the amount of $C^{14}$ trapped as $C^{14}$ bicarbonate ion. The data are presented as % activity of control in Table 3, below.

TABLE 3

Inhibition of mitochondrial fatty acid oxidation using palmitoyl carnitine as substrate - % of Control At 3 concentrations.

| Compound # | 100 μM | 30 μM | 3 μM |
|---|---|---|---|
| Ranolazine | 63% | 98% | — |
| 14 | — | — | — |
| 7 | 95% | 102% | 109% |
| 15 | 82% | 98% | 106% |
| 17 | 80% | 88% | 103% |
| 16 | 64% | | |
| 18 | 17% | | |
| 19 | — | | |
| 22 | 25% | | |
| 13 | — | — | — |

EXAMPLE 6

Metabolic Stability: As a measure of metabolic stability the compounds of this invention were incubated with human liver S-9 microsomal fractions. After, 30 minutes at 37 C, the amount of parent drug remaining was determined using LC-mass spec. The response factors for each compound was determined by establishing a standard curve and using an internal standard during the analysis of the samples. An average of five experiments for percentage of ranolazine remaining at the 30 minute time point is 57%. The compounds of this invention were assayed as described in the protocol below and the percentage of parent remaining was divided by the average % of ranolazine remaining (57%) affording a metabolic stability factor. A compound with a stability number greater than 1.2 has a better stability than ranolazine in the liver S-9 assay. A compound with a stability number between 1.2 and 0.8 has an equivalent stability in the liver S-9 assay. A compound with a stability number less than 0.8 is less stable than ranolazine in the liver S-9 assay.

The purpose of this experiment is to compare the percentages remaining for compounds of this invention with the percentage remaining for ranolazine after 30 minutes of incubation with human liver S9 fractions.

Reagents

The following reagents were used; Potassium phosphate, 0.5M pH 7.4 (incubation buffer), kept at room temperature; 0.05M $MgCl_2$ kept at 4° C.; P-Nicotinamide adenine dinucleotide phosphate, tetrasodium salt, reduced form (NADPH), 0.02M solution in water (~16.6mg/mL) from Sigma Lot #79H7044 prepared on day of use. 1 mM of ranolazine or Compounds 43, 45, 47, 52, 70, 74, 76, 78, and 80 in ACN further diluted to obtain 100 μM in 10% ACN; Human S9 stock: 20 mg/mL from Gentest.

Procedure
Incubation mixtures were prepared as follows:

TABLE 4

| Component | Volume per 0.25 mL of Incubation Mixture | Final concentration |
| --- | --- | --- |
| 10 µM CVT compounds | 25 µL | 10 µM |
| $MgCl_2$ | 25 µL | 0.005 M |
| NADPH | 25 µL | 0.002 M |
| S9 | 25 µL | 2 mg/mL |
| Incubation Buffer | 25 µL | 0.05 M |
| Water | 125 µL | — |

* 1% organic solvent (acetonitrile) was used in incubation mixture. Generally, 30 incubates were prepared at a time by pre-mixing 0.75 mL of $MgCl_2$, 0.75 mL of incubation buffer, 0.75 mL of NADPH, 3.75 mL of water. Then pipette 200 µL/incubate, add 25 µL of compound being tested, mix, and initiate reaction by addition of S-9.

Combine all components with incubation buffer and re-pipette 200 µL/tube+25 µL of the compound being tested along with 25 µL of S-9.

After 5 min of pre-incubation at 37° C., at 0 and 30 min after starting the reaction, a 50 µl aliquot of the incubation mixture was removed and added to 100 µL of 9:1 acetonitrile: methanol containing the internal standard.

The mixture was centrifuged and a 100 µL aliquot of the supernatant was diluted in 1 mL of solvent C (0.1% Formic Acid in water). Then samples were analyzed for change between the ratio of compound to internal standard at time zero and 30 minutes by LC/MS (injected 10 EL).

Analytical and Data Calculations

Samples were analyzed for the starting compounds and potential metabolite/s by LC/MS using an internal standard and an ODS-C18 column with a flow rate of 0.25 ml/min. Following the above procedure resulted in the following relative stability factors as compared to ranolazine for the compounds of this invention as illustrated in Table 3. If a compound is more stable than ranolazine than the stability factor will be greater than 1.0. If a compound is less stable than ranolazine, than the stability factor will be less than 1.0.

TABLE 4

| Compound # | Liver S9 Parent Present relative to Ranolazine |
| --- | --- |
| Ranolazine | 1.0 |
| 5 | 0.45 |
| 7 | 1.51 |
| 15 | 1.20 |
| 16 | 0.15 |
| 17 | 0.45 |

We claim:
1. A substituted piperazine compound having the following formula:

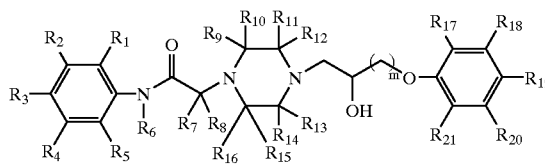

I wherein m=1 or 2;
$R_1$, $R_2$, $R_3$, $R_4$ and $R_5$ are each independently selected from the group consisting of hydrogen, halo, $CF_3$, CN, $OR_{23}$, $SR_{23}$, $N(R_{23})_2$, $SO_2N(R_{23})_2$, $COR_{23}$, $C_{1-15}$ straight or branched alkyl, $C_{2-15}$ straight or branched alkenyl, morpholino, and pyrrolyl, wherein the alkyl substituent is optionally substituted with 1 substituent selected from the group consisting of $OR_{23}$, wherein $R_2$ and $R_3$ may join together to form a fused ring system wherein the two R groups together consist of from three to four carbon atoms, and wherein $R_4$ and $R_5$ may join together to form —CH=CH—CH=CH—;

$R_6$, $R_7$ and $R_8$ are each hydrogen;

$R_9$, $R_{10}$, $R_{11}$, $R_{12}$, $R_{13}$, $R_{14}$, $R_{15}$ and $R_{16}$ are each independently selected from the group consisting of hydrogen, and $C_{1-4}$ straight or branched alkyl, wherein $R_9$ and $R_{10}$ may together form a carbonyl, or $R_{11}$ and $R_{12}$ may together form a carbonyl, or $R_{13}$ and $R_{14}$ may together form a carbonyl, or $R_{15}$ and $R_{16}$ may together form a carbonyl with the proviso that $R_9$, $R_{10}$, $R_{11}$, $R_{12}$, $R_{13}$, $R_{14}$, $R_{15}$ and $R_{16}$ are not all simultaneously hydrogen;

$R_{17}$, $R_{18}$, $R_{19}$, $R_{20}$, and $R_{21}$ are each independently selected from the group consisting of hydrogen, halo, $OR_{23}$, $C_{1-15}$ straight or branched alkyl, and phenyl; and $R_{23}$ is selected from the group consisting of H and $C_{1-15}$ straight or branched alkyl.

2. The compound of claim 1 wherein $R_1$, $R_2$, $R_3$, $R_4$, and $R_5$ are each independently selected from the group consisting of hydrogen, halo, $CF_3$, CN, $OR_{23}$, $SR_{23}$, $N(R_{23})_2$, $SO_2N(R_{23})_2$, $COR_{23}$, $C_{1-8}$ straight or branched alkyl, $C_{2-8}$ straight or branched alkenyl, morpholino, and pyrrolyl, wherein the alkyl substituent is optionally substituted with 1 substituent selected from the group consisting of $OR_{23}$, wherein $R_2$ and $R_3$ may join together to form a fused ring system wherein the two R groups together consist of from three to four carbon atoms, and wherein $R_4$ and $R_5$ may join together to form —CH=CH—CH=CH—;

$R_6$, $R_7$ and $R_8$ are each hydrogen;

$R_9$, $R_{10}$, $R_{11}$, $R_{12}$, $R_{13}$, $R_{14}$, $R_{15}$ and $R_{16}$ are each independently selected from the group consisting of hydrogen and $C_{1-4}$ straight or branched alkyl, wherein $R_9$ and $R_{10}$ may together form a carbonyl, or $R_{11}$ and $R_{12}$ may together form a carbonyl, or $R_{13}$ and $R_{14}$ may together form a carbonyl, or $R_{15}$ and $R_{16}$ may together form a carbonyl; and $R_{17}$, $R_{18}$, $R_{19}$, $R_{20}$, and $R_{21}$ are each independently selected from the group consisting of hydrogen, halo, $OR_{23}$, $C_{1-15}$ straight or branched alkyl, and phenyl.

3. The compound of claim 1 wherein $R_1$, $R_2$, $R_3$, $R_4$ and $R_5$ are each independently selected from the group consisting of hydrogen, halo, $CF_3$, CN, $OR_{23}$, $SR_{23}$, $N(R_{23})_2$, $SO_2N(R_{23})_2$, $COR_{23}$, $C_{1-6}$ straight or branched alkyl, $C_{2-6}$ straight or branched alkenyl, morpholino, and pyrrolyl, wherein the alkyl substituent is optionally substituted with 1 substituent selected from the group consisting of $OR_{23}$, wherein $R_2$ and $R_3$ may join together to form a fused ring system wherein the two R groups together consist of from three to four carbons atoms, and wherein $R_4$ and $R_5$ may join together to form —CH=CH—CH=CH—;

$R_6$, $R_7$ and $R_8$ are each hydrogen;

$R_9$, $R_{10}$, $R_{11}$, $R_{12}$, $R_{13}$, $R_{14}$, $R_{15}$ and $R_{16}$ are each independently selected from the group consisting of hydrogen and $C_{1-4}$ straight or branched alkyl, wherein $R_9$ and $R_{10}$ may together form a carbonyl, or $R_{11}$ and $R_{12}$ may together form a carbonyl, or $R_{13}$ and $R_{14}$ may together form a carbonyl, or $R_{15}$ and $R_{16}$ may together form a carbonyl;

$R_{17}$, $R_{18}$, $R_{19}$, $R_{20}$, and $R_{21}$ are each independently selected from the group consisting of hydrogen, halo, $OR_{23}$, $C_{1-15}$ straight or branched alkyl, and phenyl; and $R_{23}$ is selected from the group consisting of H and $C_{1-8}$ straight or branched alkyl.

4. The composition of claim 1 wherein $R_1$, $R_2$, $R_3$, $R_4$ and $R_5$ are each independently selected from the group consisting of hydrogen, halo, $CF_3$, CN, $OR_{23}$, $SR_{23}$, $N(R_{23})_2$, $SO_2N(R_{23})_2$, $COR_{23}$, $C_{1-6}$ straight or branched alkyl, $C_{2-6}$ straight or branched alkenyl, morpholino, and pyrrolyl, wherein the alkyl substituent is optionally substituted with 1 $OR_{23}$, wherein $R_2$ and $R_3$ may join together to form a fused ring system wherein the two R groups together consist of from three to four carbon atoms, and wherein $R_4$ and $R_5$ may join together to form —CH=CH—CH=CH—;

$R_6$, $R_7$ and $R_8$ are each hydrogen;

$R_9$, $R_{10}$, $R_{11}$, $R_{12}$, $R_{13}$, $R_{14}$, $R_{15}$ and $R_{16}$ are each independently selected from the group consisting of hydrogen and $C_{1-2}$ alkyl, wherein $R_9$ and $R_{10}$ may together form a carbonyl, or $R_{11}$ and $R_{12}$ may together form a carbonyl, or $R_{13}$ and $R_{14}$ may together form a carbonyl, or $R_{15}$ and $R_{16}$ may together form a carbonyl;

$R_{17}$, $R_{18}$, $R_{19}$, $R_{20}$, and $R_{21}$ are each independently selected from the group consisting of hydrogen, halo, $OR_{23}$, $C_{1-8}$ straight or branched alkyl, and phenyl; and $R_{23}$ is selected from the group consisting of H and $C_{1-5}$ straight or branched alkyl.

5. The compound of claim 4 wherein wherein $R_1$, $R_2$, $R_3$, $R_4$ and $R_5$ are each independently selected from the group consisting of hydrogen, halo, $CF_3$, CN, $OR_{23}$, $SR_{23}$, $N(R_{23})_2$, $SO_2N(R_{23})_2$, $COR_{23}$, $C_{1-3}$ straight or branched alkyl, $C_{2-6}$ straight or branched alkenyl, morpholino, and pyrrolyl, wherein the alkyl substituent is optionally substituted with 1 $OR_{23}$, wherein $R_2$ and $R_3$ may join together to form a fused ring system wherein the two R groups together consist of from three to four carbon atoms, and wherein $R_4$ and $R_5$ may join together to form —CH=CH—CH=CH—;

$R_6$, $R_7$ and $R_8$ are each hydrogen;

$R_9$, $R_{10}$, $R_{11}$, $R_{12}$, $R_{13}$, $R_{14}$, $R_{15}$ and $R_{16}$ are each independently selected from the group consisting of hydrogen and $C_{1-2}$ alkyl, wherein $R_9$ and $R_{10}$ may together form a carbonyl, or $R_{11}$ and $R_{12}$ may together form a carbonyl, or $R_{13}$ and $R_{14}$ may together form a carbonyl, or $R_{15}$ and $R_{16}$ may together form a carbonyl;

$R_{17}$, $R_{18}$, $R_{19}$, $R_{20}$ and $R_{21}$ are each independently selected from the group consisting of hydrogen, halo, $OR_{23}$, and $C_{1-8}$ straight or branched alkyl; and $R_{23}$ is selected from the group consisting of H and $C_{1-5}$ straight or branched alkyl.

6. The compound of claim 4 wherein $R_1$, $R_2$, $R_3$, $R_4$ and $R_5$ are each independently selected from the group consisting of hydrogen, halo, $CF_3$, CN, $OR_{23}$, $SR_{23}$, $N(R_{23})_2$, $SO_2N(R_{23})_2$, $COR_{23}$, $C_{1-3}$ straight or branched alkyl, $C_{2-6}$ straight or branched alkenyl, morpholino, and pyrrolyl, wherein the alkyl substituent is optionally substituted with 1 $OR_{23}$, wherein $R_2$ and $R_3$ may join together to form a fused ring system wherein the two R groups together consist of from three to four carbon atoms, and wherein $R_4$ and $R_5$ may join together to form —CH=CH—CH=CH—;

$R_6$, $R_7$ and $R_8$ are each hydrogen;

$R_9$, $R_{10}$, $R_{11}$, $R_{12}$, $R_{13}$, $R_{14}$, $R_{15}$ and $R_{16}$ are each independently selected from the group consisting of hydrogen and $C_{1-2}$ alkyl, wherein $R_9$ and $R_{10}$ may together form a carbonyl, or $R_{11}$ and $R_{12}$ may together form a carbonyl, or $R_{13}$ and $R_{14}$ may together form a carbonyl, or $R_{15}$ and $R_{16}$ may together form a carbonyl;

$R_{17}$, $R_{18}$, $R_{19}$, $R_{20}$ and $R_{21}$ are each independently selected from the group consisting of hydrogen, halo, $OR_{23}$, and $C_{1-8}$ straight or branched alkyl; and $R_{23}$ is selected from the group consisting of H and $C_{1-2}$ alkyl.

7. The compound of claim 4 wherein wherein $R_1$, $R_2$, $R_3$, $R_4$ and $R_5$ are each independently selected from the group consisting of hydrogen, halo, $CF_3$, CN, $OR_{23}$, $SR_{23}$, $N(R_{23})_2$, $SO_2N(R_{23})_2$, $COR_{23}$, $C_{1-3}$ straight or branched alkyl, $C_{2-3}$ straight or branched alkenyl, morpholino, and pyrrolyl, wherein the alkyl substituent is optionally substituted with 1 $OR_{23}$, wherein $R_2$ and $R_3$ may join together to form a fused ring system wherein the two R groups together consist of from three to four carbon atoms, and wherein $R_4$ and $R_5$ may join together to form —CH=CH—CH=CH—;

$R_6$, $R_7$ and $R_8$ are each hydrogen;

$R_9$, $R_{10}$, $R_{11}$, $R_{12}$, $R_{13}$, $R_{14}$, $R_{15}$ and $R_{16}$ are each independently selected from the group consisting of hydrogen and methyl, wherein $R_9$ and $R_{10}$ may together form a carbonyl, or $R_{11}$ and $R_{12}$ may together form a carbonyl, or $R_{13}$ and $R_{14}$ may together form a carbonyl;

$R_{17}$, $R_{18}$, $R_{19}$, $R_{20}$ and $R_{21}$ are each independently selected from the group consisting of hydrogen, halo, $OR_{23}$ and $C_{1-2}$ alkyl; and $R_{23}$ is selected from the group consisting of H and methyl.

8. The compound of claim 7 wherein $R_{18}$, $R_{19}$, $R_{20}$, and $R_{21}$ are each hydrogen and $R_{17}$ is halo or $OR_{23}$.

9. The compound of claim 8 wherein $R_{12}$ is (S) methyl and $R_9$, $R_{10}$, $R_{11}$, $R_{13}$, $R_{14}$, $R_{15}$ and $R_{16}$ are each hydrogen.

10. The compound of claim 8 wherein $R_9$ and $R_{10}$ together form a carbonyl and $R_{11}$, $R_{12}$, $R_{13}$, R, $R_{15}$ and R are each hydrogen.

11. The compound of claim 8 wherein $R_9$, $R_{10}$, $R_{11}$, $R_{12}$, $R_{15}$ and $R_{16}$ are each hydrogen and $R_{13}$ and $R_{14}$ together form a carbonyl.

12. The compound of claim 2 or 3 or 4 or 5 or 6 or 7 or 8 or 9 or 10 or 11 wherein m=1.

13. The compound of claim 8 wherein $R_1$, $R_2$, $R_3$, $R_4$ and $R_5$ are each independently selected from the group consisting of hydrogen, halo, $CF_3$, CN, $OR_{23}$, $SR_{23}$, $N(R_{23})_2$, $SO_2N(R_{23})_2$, $COR_{23}$, $C_{1-3}$ straight or branched alkyl, $C_{2-3}$ straight or branched alkenyl, N-morpholino, and pyrrolyl, wherein the alkyl substituent is optionally substituted with 1 OH, wherein $R_2$ and $R_3$ may join together to form a fused ring system wherein the two R groups together consist of three carbon atoms, and wherein $R_4$ and $R_5$ may join together to form —CH=CH—CH=CH—.

14. The compound of claim 1 wherein m=1 or 2;

$R_1$, $R_2$, $R_3$, $R_4$ and $R_5$ are each independently selected from the group consisting of hydrogen, halo, $CF_3$, $OR_{23}$ and $C_{1-2}$ alkyl;

$R_6$, $R_7$ and $R_8$ are each hydrogen;

$R_9$, $R_{10}$, $R_{11}$, $R_{12}$, $R_{13}$, $R_{14}$, $R_{15}$ and $R_{16}$ are each independently selected from the group consisting of hydrogen and $C_{1-4}$ straight or branched alkyl, or $R_9$ and $R_{10}$ may together form a carbonyl, or $R_{11}$ and $R_{12}$ may together form a carbonyl, or $R_{13}$ and $R_{14}$ may together form a carbonyl, or $R_{15}$ and $R_{16}$ may together form a carbonyl with the proviso that $R_9$, $R_{10}$, $R_{11}$, $R_{12}$, $R_{13}$, $R_{14}$, $R_{15}$ and $R_{16}$ are not all simultaneously hydrogen;

$R_{17}$, $R_{18}$, $R_{19}$, $R_{20}$, and $R_{21}$ are each independently selected from the group consisting of hydrogen, halo, $OR_{23}$, $C_{1-4}$ straight or branched alkyl, and phenyl; and wherein $R_{23}$ is a $C_{1-2}$ alkyl.

15. The compound of claim 14 wherein $R_1$, $R_2$, $R_3$, $R_4$ and $R_5$ are each independently selected from the group consisting of hydrogen and methyl.

16. The compound of claim 14 wherein $R_9$, $R_{10}$, $R_{11}$, $R_{12}$, $R_{13}$, $R_{14}$, $R_{15}$ and $R_{16}$ are each independently selected from the group consisting of hydrogen and $C_{1-2}$ alkyl, or $R_9$ and $R_{10}$ may together form a carbonyl, or $R_{15}$ and $R_{16}$ may together form a carbonyl with the proviso that $R_9$, $R_{10}$, $R_{11}$, $R_{12}$, $R_{13}$, $R_{14}$, $R_{15}$ and $R_{16}$ are not all simultaneously hydrogen.

17. The compound of claim 14 wherein $R_9$ and $R_{10}$ together form a carbonyl or $R_{15}$ and $R_{16}$ together form a carbonyl or both $R_9$ and $R_{10}$ together form a carbonyl and $R_{15}$ and $R_{16}$ together form a carbonyl.

18. The compound of claim 14 wherein $R_{17}$, $R_{18}$, $R_{19}$, $R_{20}$ and $R_{21}$ are each independently selected from the group consisting of hydrogen, halo and $C_{1-4}$ straight or branched alkyl and $OR_{23}$, wherein $R_{23}$ is $C_{1-2}$ alkyl.

19. The compound of claim 1 wherein m=1;
$R_1$, $R_2$, $R_3$, $R_4$ and $R_5$ are each independently selected from the group consisting of hydrogen, and methyl;
$R_6$, $R_7$ and $R_8$ are each hydrogen; $R_9$, $R_{10}$, $R_{11}$, $R_{12}$, $R_{13}$, $R_{14}$, $R_{15}$ and $R_{16}$ are each independently selected from the group consisting of hydrogen and $C_{1-4}$ straight or branched alkyl, or $R_9$ and $R_{10}$ may together form a carbonyl, or $R_{11}$ and $R_{12}$ may together form a carbonyl, or $R_{13}$ and $R_{14}$ may together form a carbonyl, or $R_{15}$ and $R_{16}$ may together form a carbonyl with the proviso that $R_9$, $R_{10}$, $R_{11}$, $R_{12}$, $R_{13}$, $R_{14}$, $R_{15}$ and $R_{16}$ are not all simultaneously hydrogen;
$R_{17}$, $R_{18}$, $R_{19}$, $R_{20}$ and $R_{21}$ are each independently selected from the group consisting of hydrogen, halo, $C_{1-4}$ straight or branched alkyl and $OR_{23}$; and
$R_{23}$ is $C_{1-2}$ alkyl.

20. The compound of claim 19 wherein $R_1$ and $R_5$ are each methyl and $R_2$, $R_3$, and $R_4$ are each hydrogen.

21. The compound of claim 19 wherein $R_{11}$, $R_{12}$, $R_{13}$, $R_{14}$, $R_{15}$ and $R_{16}$ are each hydrogen and $R_9$ and $R_{10}$ together form carbonyl.

22. The compound of claim 19 wherein $R_9$, $R_{10}$, $R_{11}$, $R_{12}$, $R_{15}$ and $R_{16}$ are each hydrogen and $R_{13}$ and $R_{14}$ together form carbonyl.

23. The compound of claim 19 wherein $R_9$, $R_{10}$, $R_{11}$, $R_{12}$, $R_{13}$, $R_{14}$, $R_{15}$ and $R_{16}$ are each independently selected from the group consisting of hydrogen and methyl.

24. The compound of claim 19 wherein, $R_{18}$, $R_{19}$ and $R_{21}$ are each hydrogen and $R_{17}$ and $R_{18}$ are each methyl.

25. The compound of claim 19 wherein, $R_{17}$, is —OCH$_3$, and $R_{18}$, $R_{19}$, $R_{20}$ and $R_{21}$ are each hydrogen.

26. The compound of claim 14 wherein, $R_{17}$, $R_{18}$, $R_{20}$ and are each hydrogen and $R_{19}$ is selected from the group consisting of —OCH$_3$, —F, $C_{1-4}$ straight or branched alkyl and phenyl.

27. The compound of claim 1 selected from the group consisting of

N-(2,6-dimethylphenyl)-2-{4-[2-hydroxy-3-(2-methoxyphenoxy)propyl]-3 oxopiperazinyl}acetamide, N-(2,6-dimethylphenyl)-2-{4-[2-hydroxy-3-(2-methoxyphenoxy)propyl]-3,5-dimethylpiperazinyl}acetamide, 2-{(5S,2R)-4-[2-hydroxy-3-(2-methoxyphenoxy)propyl]-2,5-dimethylpiperazinyl}-N-(2,6-dimethylphenyl) acetamide, N-(2,6-dimethylphenyl)-2-{4-[2-hydroxy-3-(2-methoxyphenoxy)propyl]-2-oxopiperazinyl}acetamide, N-(2,6-dimethylphenyl)-2-{4-[2-hydroxy-3-(2 methoxyphenoxy)propyl]-3,3-dimethylpiperazinyl}acetamide, N-(2,6-dimethylphenyl)-2-{4-[2-hydroxy-4-(2-methoxyphenoxy)butyl]-piperazinyl}acetamide, N-(2,6-dimethylphenyl)-2-{4-[4-(4-fluorophenoxy)-2-hydroxybutyl]-piperazinyl}acetamide, 2-(4-{4-[4-(tert-butyl)phenoxy]-2-hydroxybutyl}piperazinyl)-N-(2,6-dimethylphenyl) acetamide, N-(2,6-dimethylphenyl)-2-{4-[2-hydroxy-4-(4-phenylphenoxy)butyl]piperazinyl}acetamide, N-(2,6-dimethylphenyl)-2-{4-[2-hydroxy-4-(4-methoxyphenoxy)butyl]-piperazinyl}acetamide, 2-{(3S)-4-[(2S)-3-(2-fluorophenoxy)-2-hydroxypropyl]-3-methylpiperazinyl}-N-(2,6-dimethylphenyl) acetamide, 2-{(3S)-4-[(2S)-3-(2-fluorophenoxy)-2-hydroxypropyl]-3-methylpiperazinyl}-N-(2,6-dichlorophenyl) acetamide, 2-{(3S)-4-[(2S)-3-(2-fluorophenoxy)-2-hydroxypropyl]-3-methylpiperazinyl}-N-(4-sulfamoylphenyl) acetamide, 2-{(3S)-4-[(2S)-3-(2-fluorophenoxy)-2-hydroxypropyl]-3-methylpiperazinyl}-N-(5-methoxy-3-(trifluoromethyl)phenyl]acetamide, 2-{(3S)-4-[(2S)-3-(2-fluorophenoxy)-2-hydroxypropyl]-3-methylpiperazinyl}-N-indan-5-ylacetamide, 2-{(3S)-4-[(2S)-3-(2-fluorophenoxy)-2-hydroxypropyl]-3-methylpiperazinyl}-N-naphthylacetamide, 2-{(3S)-4-[(2S)-3-(2-fluorophenoxy)-2-hydroxypropyl]-3-methylpiperazinyl}-N-(4-chloronaphthyl) acetamide, 2-{(3S)-4-[(2S)-3-(2-fluorophenoxy)-2-hydroxypropyl]-3-methylpiperazinyl}-N-(2-pyrrolylphenyl) acetamide, 2-{(3S)-4-[(2S)-3-(2-fluorophenoxy)-2-hydroxypropyl]-3-methylpiperazinyl}-N-phenylacetamide, 2-{(3S)-4-[(2S)-3-(2-fluorophenoxy)-2-hydroxypropyl]-3-methylpiperazinyl}-N-(2-chlorophenyl) acetamide, 2-{(3S)-4-[(2S)-3-(2-fluorophenoxy)-2-hydroxypropyl]-3-methylpiperazinyl}-N-(2-chloro-4-methylphenyl) acetamide, 2-{(3S)-4-[(2S)-3-(2-fluorophenoxy)-2-hydroxypropyl]-3-methylpiperazinyl}-N-[2-(1-methylvinyl)phenyl] acetamide, 2-{(3S)-4-[(2S)-3-(2-fluorophenoxy)-2-hydroxypropyl]-3-methylpiperazinyl}-N-(2-methylphenyl) acetamide, 2-{(3S)-4-[(2S)-3-(2-fluorophenoxy)-2-hydroxypropyl]-3-methylpiperazinyl}-N-[6-methyl-2-(isopropyl) phenyl]acetamide, 2-{(3S)-4-[(2S)-3-(2-fluorophenoxy)-2-hydroxypropyl]-3-methylpiperazinyl}-N-(3-methylthiophenyl) acetamide, 2-{(3S)-4-[(2S)-3-(2-fluorophenoxy)-2-hydroxypropyl]-3-methylpiperazinyl}-N-(4-chloro-2-methoxy-5-methylphenyl) acetamide, 2-{(3S)-4-[(2S)-3-(2-fluorophenoxy)-2-hydroxypropyl]-3-methylpiperazinyl}-N-[4-(dimethylamino) phenyl] acetamide, 2-{(3S)-4-[(2S)-3-(2-fluorophenoxy)-2-hydroxypropyl]-3-methylpiperazinyl}-N-(2,4-dimethoxyphenyl) acetamide, 2-{(3S)-4-[(2S)-3-(2-fluorophenoxy)-2-hydroxypropyl]-3-methylpiperazinyl}-N-(3,4-dichlorophenyl) acetamide, 2-{(3S)-4-[(2S)-3-(2-fluorophenoxy)-2-hydroxypropyl]-3-methylpiperazinyl}-N-(4-chlorophenyl) acetamide, 2-{(3S)-4-[(2S)-3-(2-fluorophenoxy)-2-hydroxypropyl]-3-methylpiperazinyl}-N-(3-chlorophenyl) acetamide, 2-{(3S)-4-[(2S)-3-(2-fluorophenoxy)-2-hydroxypropyl]-3-methylpiperazinyl}-N-(3,5-dichlorophenyl) acetamide, 2-{(3S)-4-[(2S)-3-(2-fluorophenoxy)-2-hydroxypropyl]-3-methylpiperazinyl}-N-(4-methoxyphenyl) acetamide, 2-{(3S)-4-[(2S)-3-(2-fluorophenoxy)-2-hydroxypropyl]-3-methylpiperazinyl}-N-(4-methylphenyl) acetamide, 2-{(3S)-4-[(2S)-3-(2-fluorophenoxy)-2-hydroxypropyl]-3-methylpiperazinyl}-N-(3-methylphenyl) acetamide, 2-{(3S)-4-[(2S)-3-(2-fluorophenoxy)-2-hydroxypropyl]-3-methylpiperazinyl}-N-(4-fluorophenyl) acetamide, 2-{(3S)-4-[(2S)-3-(2-fluorophenoxy)-2-hydroxypropyl]-3-methylpiperazinyl}-N-(4-cyanophenyl) acetamide, 2-{(3S)-4-[(2S)-3-(2-fluorophenoxy)-2-hydroxypropyl]-3-methylpiperazinyl}-N-(4-acetylphenyl) acetamide, 2-{(3S)-4-[(2S)-3-(2-fluorophenoxy)-2-hydroxypropyl]-3-methylpiperazinyl}-N-(2-methoxyphenyl) acetamide, 2-{(3S)-4-[(2S)-3-(2-fluorophenoxy)-2-hydroxypropyl]-3-methylpiperazinyl}-N-[4-(trifluoromethyl)phenyl] acetamide, 2-{(3S)-4-[(2S)-3-(2-fluorophenoxy)-2-hydroxypropyl]-3-methylpiperazinyl}-N-[4-chloro-3-(trifluoromethyl)phenyl]acetamide, 2-{(3S)-4-[(2S)-3-(2-fluorophenoxy)-2-hydroxypropyl]-3-methylpiperazinyl}-N-(3,5-dimethoxyphenyl) acetamide, 2-{(3S)-4-[(2S)-3-(2-fluorophenoxy)-2-hydroxypropyl]-3-methylpiperazinyl}-N-(4-morpholin-4-ylphenyl) acetamide, 2-{(3S)-4-[(2S)-3-(2-fluorophenoxy)-2-hydroxypropyl]-3-methylpiperazinyl}-N-(3-fluoro-4-methoxyphenyl) acetamide, 2-{(3S)-4-[(2S)-3-(2-fluorophenoxy)-2-hydroxypropyl]-3-methylpiperazinyl}-N-(3,4,5-trimethoxyphenyl) acetamide, 2-{(3S)-4-[(2S)-3-(2-fluorophenoxy)-2-hydroxypropyl]-3-methylpiperazinyl}-N-(3,4-dimethoxyphenyl) acetamide, 2-{(3S)-4-[(2S)-3-(2-fluorophenoxy)-2-hydroxypropyl]-3-methylpiperazinyl}-N-(4-chloro-2-fluorophenyl) acetamide, and 2-{(3S)-4-[(2S)-3-(2-fluorophenoxy)-2-hydroxypropyl]-3-methylpiperazinyl}-N-[2-(hydroxymethyl)-6-methylphenyl]acetamide.

28. A method of treatment comprising administering a therapeutically effective amount of a compound of claim 1 to a mammal in need of a treatment selected from the group consisting of protecting skeletal muscles against damage resulting from trauma, protecting skeletal muscles subsequent to muscle or systemic diseases, treating shock conditions, preserving donor tissue and organs used in transplants, and treating cardiovascular diseases.

29. The method of claim 28 wherein the cardiovascular disease is selected from the group consisting of atrial and ventricular arrhythmias, Prinzmetal's (variant) angina, stable angina, exercise induced angina, congestive heart disease, and myocardial infarction.

30. The method of claim 28 wherein the therapeutically effective amount ranges from about 0.01 to about 100 mg/kg weight of the mammal.

31. The method of claim 28 wherein the mammal is a human.

32. A pharmaceutical composition of matter comprising the compound of claim 1 and one or more pharmaceutical excipients.

33. The pharmaceutical composition of matter of claim 32 wherein the pharmaceutical composition is in the form of a solution.

34. The pharmaceutical composition of matter of claim 32 wherein the pharmaceutical composition is in a form selected from the group consisting of a tablet and a capsule.

* * * * *

UNITED STATES PATENT AND TRADEMARK OFFICE
CERTIFICATE OF CORRECTION

PATENT NO. : 6,677,336 B2  Page 1 of 1
DATED : January 13, 2004
INVENTOR(S) : Zablocki et al.

It is certified that error appears in the above-identified patent and that said Letters Patent is hereby corrected as shown below:

<u>Column 31</u>,
Line 16, delete "$_{R9}$" and replace with -- $R_9$ --.

Signed and Sealed this

Thirtieth Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,677,336 B2
DATED : January 13, 2004
INVENTOR(S) : Zablocki et al.

It is certified that error appears in the above-identified patent and that said Letters Patent is hereby corrected as shown below:

Column 30,
Line 29, delete "$R_{11}$, $R_{12}$, $R_{13}$, R, $R_{15}$ and R" and replace with
-- $R_{11}$, $R_{12}$, $R_{13}$, $R_{14}$, $R_{15}$ and $R_{16}$ --.

Signed and Sealed this

Thirty-first Day of August, 2004

JON W. DUDAS
*Director of the United States Patent and Trademark Office*

UNITED STATES PATENT AND TRADEMARK OFFICE
CERTIFICATE OF CORRECTION

PATENT NO. : 6,677,336 B2
APPLICATION NO. : 09/791134
DATED : January 13, 2004
INVENTOR(S) : Zablocki et al.

Page 1 of 1

It is certified that error appears in the above-identified patent and that said Letters Patent is hereby corrected as shown below:

At Column 31, line 41 of claim 24 delete the line

"are each hydrogen and R(sub)17 and R(sub)18 are each methyl"

and replace it with

--are each hydrogen and R(sub)17 and R(sub)20 are each methyl--

At Column 32, line 21 of claim 27 delete the line

"3-methylpiperazinyl}-N-(5-methoxy-3-"

and replace it with

--3-methylpiperazinyl}-N-[5-methoxy-3- --

Signed and Sealed this

Sixteenth Day of September, 2008

JON W. DUDAS
*Director of the United States Patent and Trademark Office*

UNITED STATES PATENT AND TRADEMARK OFFICE
CERTIFICATE OF CORRECTION

PATENT NO. : 6,677,336 B2
APPLICATION NO. : 09/791134
DATED : January 13, 2004
INVENTOR(S) : Zablocki et al.

Page 1 of 1

It is certified that error appears in the above-identified patent and that said Letters Patent is hereby corrected as shown below:

At Column 31, line 44 of Claim 26 delete the line

"The compound of claim 14 wherein R(sub)17, R(sub)18, R(sub)20 and"

and replace it with

"The compound of claim 14 wherein R(sub)17, R(sub)18, R(sub)20 and R(sub)21"

Signed and Sealed this

Tenth Day of March, 2009

JOHN DOLL
*Acting Director of the United States Patent and Trademark Office*